US012237089B2

(12) United States Patent
Schein et al.

(10) Patent No.: US 12,237,089 B2
(45) Date of Patent: Feb. 25, 2025

(54) ONLINE MONITORING OF CLINICAL DATA DRIFTS

(71) Applicant: GE Precision Healthcare LLC, Milwaukee, WI (US)

(72) Inventors: Sagi Schein, Kiryat Tivon (IL); Ole Jakob Utkilen, Tel Aviv (IL); Ruth Bergman, Ceasarea (IL); Eyal Hayun, Adi (IL); Edwar Bkheet, Haifa (IL); Antonio Zaitoun, Haifa (IL); Vitaly Burshtein, Kiryat Ata (IL)

(73) Assignee: GE Precision Healthcare LLC, Waukesha, WI (US)

(\*) Notice: Subject to any disclaimer, the term of this patent is extended or adjusted under 35 U.S.C. 154(b) by 393 days.

(21) Appl. No.: 17/645,892

(22) Filed: Dec. 23, 2021

(65) Prior Publication Data

US 2023/0207138 A1 Jun. 29, 2023

(51) Int. Cl.
*G16H 50/70* (2018.01)
*G06F 40/20* (2020.01)
*G08B 21/18* (2006.01)

(52) U.S. Cl.
CPC ............. *G16H 50/70* (2018.01); *G06F 40/20* (2020.01); *G08B 21/182* (2013.01)

(58) Field of Classification Search
None
See application file for complete search history.

(56) References Cited

U.S. PATENT DOCUMENTS

| 9,659,063 | B2 | 5/2017 | Cammert et al. |
| 2005/0096866 | A1* | 5/2005 | Shan ................... G06F 11/0751 |
| | | | 702/179 |
| 2017/0373981 | A1* | 12/2017 | Sasak ................... H04L 47/283 |

(Continued)

FOREIGN PATENT DOCUMENTS

EP 2149100 A1 2/2010

OTHER PUBLICATIONS

International Application No. PCT/US2022/053398 filed Dec. 19, 2022—International Search Report and Written Opinion issued on Apr. 7, 2023; 15 pages.

(Continued)

*Primary Examiner* — Stella Higgs
(74) *Attorney, Agent, or Firm* — Amin, Turocy & Watson, LLP

(57) ABSTRACT

Techniques are described that facilitate online monitoring of clinical data streams in association with detecting missing data and other suspicious data deviations. According to an embodiment, a computer implemented comprises receiving, by a system comprising a processor, a data stream from a plurality of different clinical data information systems configured to report defined clinical events within the data stream and recording arrival times of received events of the defined clinical events. The method further comprises detecting, by the system, data failure events associated with the data stream based on time differences between the arrival times for defined clinical events of the same type and estimated probabilities that the time differences are expected, wherein the detecting comprises estimating the probabilities that the time differences are expected using time-to-event models developed for each of the defined clinical events of the same type.

20 Claims, 11 Drawing Sheets

(56) References Cited

U.S. PATENT DOCUMENTS

2018/0122506 A1    5/2018    Grantcharov et al.
2021/0019300 A1    1/2021    Marathe
2021/0076966 A1    3/2021    Grantcharov

OTHER PUBLICATIONS

Rivetti, N. et al. | "Probabilistic Management of Late Arrival of Events". (2018) 52-63. doi 10.1145/3210284.3210293, 13 pages.

UMLS | "Unified Medical Language System (UMLS)", webpage https://www.nlm.nih.gov/research/umls/index.html, last accessed on Nov. 10, 2021, 2 pages.

Wikipedia | "Weibull distribution", webpage https://en.wikipedia.org/wiki/Weibull_distribution, last accessed Nov. 10, 2021, 11 pages.

Wikipedia | "Survival function", webpage hhttps://en.wikipedia.org/wiki/Survival_function, last accessed Nov. 10, 2021, 9 pages.

* cited by examiner

ONLINE MONITORING OF CLINICAL DATA DRIFTS

TECHNICAL FIELD

This application relates to online monitoring of clinical data streams in association with detecting missing data and other suspicious data deviations.

BACKGROUND

Many clinical applications used in active hospital environment process clinical data streamed in real-time from various disparate electronic clinical data sources. For example, in a hospital environment, multiple electronic information systems typically stream such data through a single gateway which standardize it into a single data feed. From the perspective of its end user, such an application should always reflect a synchronized view of the patients' data, possibly up to some unavoidable time skew. Unfortunately, information systems may suffer intermittent and unexpected failures due electricity or network outages, equipment malfunctions or software bugs. Such failures may be quite nuanced and difficult to notice. For example, suppose one of the central lab's systems is taken offline. From the user perspective, results for some of the samples are simply delayed unexpectedly where in fact they might become unavailable. Failing to detect such failures may result in a potential damage to patients or infringing the service level agreement (SLA) of the application. Existing systems typically implement a manual monitoring procedure in which a qualified subject matter expert (SME) inspects the incoming data stream to detect when data may be missing and raise an alert. However, such a manual monitoring approach cannot scale to multiple customers and a high frequency data rate.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described herein that facilitate online monitoring of clinical data streams in association with detecting missing data and other suspicious data deviations.

According to an embodiment, a system is provided that comprises a memory that stores computer executable components, and a processor that executes the computer executable components stored in the memory. The computer executable components comprise a reception component that receives a data stream from a plurality of different clinical data information systems configured to report defined clinical events within the data stream, wherein the reception component timestamps arrival times of received events of the defined clinical events. The computer executable components further comprise a detection component that monitors the data stream and detects data failure events associated with the data stream based on time differences between the arrival times for defined clinical events of the same type and estimated probabilities that the time differences are expected, wherein the detection component estimates the probabilities that the time differences are expected using time-to-event models developed for each of the defined clinical events of the same type. The computer executable components further comprise an alert component that generates data failure alerts in response to detection of the data failure events and provides the data failure alerts to one or more defined entities using one or more electronic notification mechanisms.

In some embodiments, elements described in connection with the disclosed systems can be embodied in different forms such as a computer-implemented method, a computer program product, or another form.

DETAILED DESCRIPTION

Figure 1:
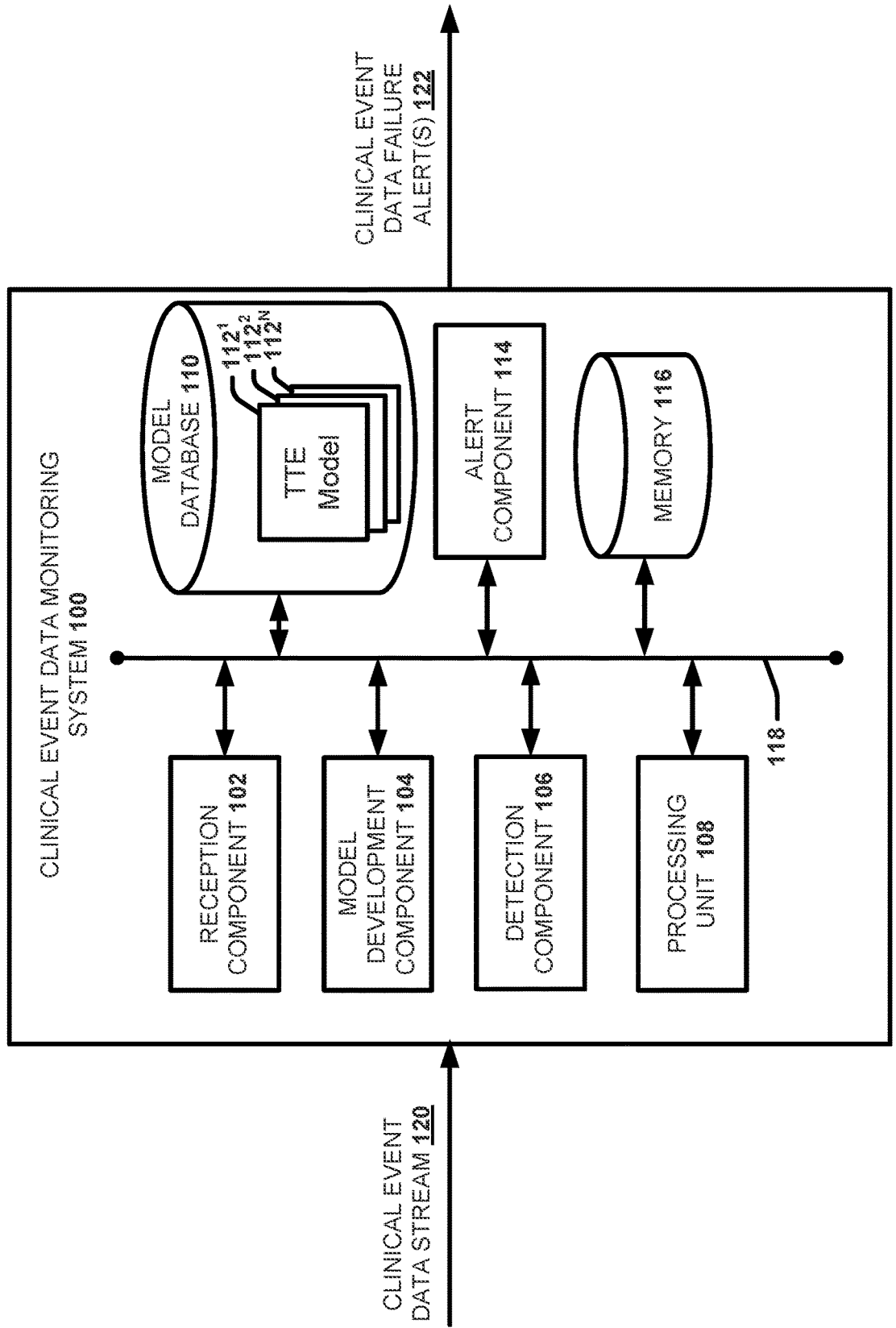
FIG. 1 illustrates a block diagram of an example, non-limiting system that facilitates online monitoring of clinical data drifts in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

As discussed above, medical data ingestion processes in an active hospital environment must cope with input variations. For example, data feeds may go down, a data generator device may yield erroneous values or stop working, data formats may change, or some non-systemic human errors may occur. These variations may cause failures to the ingestion process or worse go unnoticed and cause a divergence between the internal hospital data systems and the external medical systems.

With this problem in mind, the disclosed subject matter provides automated tools for detecting such failures in data transmissions between hospital information technology (IT) systems and an external application which depends on the data. The data failures can include missing or late data, as well as other types of data errors, such as formatting errors, improper data values and the like. This disclosed techniques thus address the case in which parts of a patient's data fails to arrive to the external application or is unreasonably delayed and provides tools and algorithms to detect and alert the operations engineers of suspected absent data so that end users can be promptly notified and remediation activities could be promptly initiated. The disclosed techniques can identify partial and total data failures in which parts or all of the clinical data stops to arrive or is greatly delayed. Such partial cases are difficult to recognize from the outside of the hospital IT environment and conventionally require manual monitoring by a SME to ensure that an agreed SLA is always maintained.

To facilitate this end, the disclosed technique provide an online monitoring system that intercepts a live data stream of clinical event data transmitted from one or more clinical data sources/system to an external consuming application. For example, assume the data an external clinical application consumes all (part of) the patient data which reside one or more hospital IT systems. This data is parsed into a stream of resources which records all medical procedures, vital signs, labs tests, and medications that patients receive over their hospital stay, as well as administrative information such as admission and discharge states. The information is sent as a stream of resources which include time of occurrence, resource type, value, unit of measure and more. From the stream of data, the application can receive essentially all (part) of the data the hospital has on the patient. In one or more embodiments, the online monitoring system simplifies this data model and only considers a stream of resources types with their time stamp and denotes each occurrence as an event. For example, one clinical event may correspond to a reported vital sign from a medical monitoring device worn by a patient, another clinical event may correspond to a reported laboratory result for the patient from a specific laboratory, another clinical event may correspond to a reported completed medical procedure for the patient received from a medical procedure recording system, and so on. In this regard, the online monitoring system defines known clinical data objects that expected to be reported in the clinical data stream as clinical events. The level of granularity of the defined clinical events can vary.

In various embodiments, the defined clinical events are taken from a defined clinical ontology such as the Unified Medical Language System (UMLS) or a similar clinical ontology. A clinical ontology aims to arrange medical knowledge in a large graph structure where nodes hold medical terms, and connecting edges define the relation between nodes. In the UMLS and other ontologies, the most common relation is the abstraction relation, also referred to as an is-a relation. In an abstraction relation, general concepts point to more specific concepts. In most cases, the events that are received in the data stream reflect specific medicine or medical procedures that are provided to patients over their course of inpatient (and/or outpatient) treatment.

Assuming a stream of medical events taken from a well-defined ontology of clinical concepts, the disclosed subject matter applies principles of machine learning and artificial intelligence to learn and characterize the statistics of the time-to-event for each clinical concept and alert when the likelihood of an actual time-to-event for a specific concept drops below a specified threshold. In particular, to predict when events are likely to be missing, the disclosed techniques model their expected arrival times in a time-to-event (TTE) model. The TTE model estimates the expected time between two events of the same type. A separate TTE model is created for each known clinical event to be reported in the data stream. The disclosed techniques further combine the TTE model with a survival analysis function to estimate the probability that an associated event time difference is appropriate or not. The survival function is a function that gives the probability that a patient, device, or other object of interest will survive beyond any specified time. In this case, we interpret it as the likelihood that an associated event time difference is at least of that long.

To generate the training data for the TTE models, for each event type, the system records the time between consecutive arrivals of the same event type and the related time differences are computed. Once enough training data to form robust statistics has been generated for a given event, the system trains the TTE models using the training data to estimate the probabilities that observed time differences between consecutive arrivals of events of the same type are expected. To facilitate this end, the system models the probability distribution of time differences for the event type. The sequence of time differences per event type represents a random process that may be modeled using parametric distributions and/or non-probability distributions. In one or more embodiments, the system can employ a Weibull distribution model to fit the time-to-event data, that is, to model the probability distribution of time differences per event type. In other embodiments, the system can employ a non-parametric model to model the probability distribution of time difference per event type, such as Parzen windows probability density estimation or the like. During the online phase (upon completion of model training) the system is triggered repeatedly once every predefined amount of time (e.g., once every minute, every 10 minutes, every 30 minutes, every hour, etc.). On activation, the system computes the time difference from the last occurrence of each event type. Then, for the corresponding TTE model, the value of the survival function is computed. If this value is below a threshold, a counter of missing events candidates for that even model is raised by one. The missing data alerts are further summed for over a defined timeslot (e.g., every 30 minutes, every hour) and an alert for that evet type is raised when the count is above a predefined threshold. This sequential voting mechanism adapts to both the severity (number of impacted concepts) and length of time concepts fail to arrive. Additionally, or alternatively, the system can sum all missing data candidate values across all (or a group) of events so that the system can react faster to large scale data drops. Such a scheme is also less prone to false alarms at the cost of lesser reporting granularity.

As some of the clinical concepts appear rarely while others have synonymous concepts, establishing robust statistics can become challenging. To address this concern, the disclose techniques further define several abstraction mechanisms for clustering similar medical events together to improved inference robustness. Concepts in such clusters can share similar data generation mechanisms and could hint on shared failures. During the training phase, instead of training for each input event, the system fits a model for each event type cluster. During the online phase, for each input event its cluster identity is identified and the proper model which represents that cluster is queried and applied. In some embodiments, a manual clustering tool is provided that enables operations engineers to manually tell the system which events types may go together. Additionally, or alternatively, the clustering can be defined based on the originating IT system. Further, the disclosed techniques propose to utilize the clinical ontology to automatically (e.g., using one or more clustering algorithms such as k-means) or semi-automatically (e.g., using some manual input) cluster the clinical event types.

The terms "algorithm" and "model" are used herein interchangeably unless context warrants particular distinction amongst the terms. The terms "AI model" and "ML model" are used herein interchangeably unless context warrants particular distinction amongst the terms.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a block diagram of an example, non-limiting clinical event data monitoring system 100 (hereinafter system 100) that facilitates online monitoring of clinical data drifts in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

In this regard, system 100 includes reception component 102, model development component 104, detection component 106, and alert component 114, all of which can be or include machine-executable components embodied within one or more machines (e.g., embodied in one or more computer-readable storage media associated with one or more machines), which when executed by the one or more machines (e.g., processors, computers, computing devices, virtual machines, etc.) can cause the one or more machines to perform the operations described. System 100 further includes a model database 110 that can include a plurality of time-to-event (TTE) models, respectively identified as TTE models $112_{1-N}$. As described in greater detail infra, these TTE models $112_{1-N}$ can respectively correspond to computer executable models or algorithms adapted to forecast the expected time between two clinical events of the same type. A separate TTE model can be generated for each defined clinical event to be monitored in the clinical event data stream 120. In this regard, the clinical event data monitoring system 100 can be any suitable machine that can execute one or more of the operations described with reference to the reception component 102, the model development component 104, the detection component 106, the alert component 114, the TTE models $112_{1-N}$, and other components described herein.

As used herein, the machine can be and/or can include one or more of a computing device, a general-purpose computer, a special-purpose computer, a quantum computing device (e.g., a quantum computer), a tablet computing device, a handheld device, a server class computing machine and/or database, a laptop computer, a notebook computer, a desktop computer, a cell phone, a smart phone, a consumer appliance and/or instrumentation, an industrial and/or commercial device, a digital assistant, a multimedia Internet-enabled phone and/or another type of device. System 100 can also be or correspond to one or more real or virtual (e.g., cloud-based) computing devices. System 100 can further include or be operatively coupled to a least one memory 116 that stores the computer executable components (e.g., the reception component 102, the model development component 104, the detection component 106, the alert component 114, the TTE models $112_{1-N}$, and other components described herein). The memory 116 can also store any information received by the system 100 (e.g., the information included in the clinical event data stream 120) and/or generated by the system 100 (e.g., clinical event data failure alters 122). System 100 can further include or be operatively coupled to at least one processing unit 108 (or processor) that executes the computer-executable components stored in the memory 116, and a system bus 118 that communicatively couples the respective components of the system 100 to one another. Examples of said memory 116 and processing unit 108 as well as other suitable computer or computing-based elements, can be found with reference to FIG. 10 (e.g., with reference to processing unit 1104 and system memory 1106), and can be used in connection with implementing one or more of the systems or components shown and described in connection with FIG. 1 or other figures disclosed herein.

The deployment architecture of system 100 can vary. In some embodiments, system 100 can be deployed a local computing device. In other embodiments, one or more of the components of system 100 can be deployed in a cloud architecture, a virtualized enterprise architecture, or an enterprise architecture wherein one the front-end components and the back-end components are distributed in a client/server relationship. With these embodiments, the features and functionalities of one or more of the reception component 102, the model development component 104, the detection component 106, the alert component 114, the TTE models $112_{1-N}$, the processing unit 108 and the memory 116 (and other components described herein), can be deployed as a web-application, a cloud-application, a thin client application, a thick client application, a native client application, a hybrid client application, or the like. Various example deployment architectures for system 100 (and other systems described herein) are described infra with reference to FIGS. 10-11.

The clinical event data monitoring system 100 is configured to monitor a clinical event data stream 120 in real-time to detect and alert of suspicious data deviations, such as missing or late data and other data deviations. In this regard, system 100 can be integrated into the medical data ingestion pipeline between the one or more data sources that provide the information included in the clinical event data stream 120 and the entity that consumes the information included the clinical event data stream 120, such as a clinical application. The specific types of data to be reported in the clinical event data stream 120 and the manner in which the consuming entity (e.g., a clinical application, system or device) is adapted to use the data can vary. For example, in the context of a hospital system, assume the clinical application is adapted to process a plurality of disparate types of clinical data reported from different hospital information systems in real-time related to patients and their medical treatment to determine how to optimize provision of care to the patients in real-time. For instance, the clinical application may be adapted to determine how to best allocate resources (e.g., staff, bed assignments, unit assignments, medical equipment and supplies, etc., prioritize patients for treatment, or plan discharge events. In accordance with this example, the clinical data may include tracked patient data for all (or a defined group of) patients from the point of admission to the point of discharge regarding their physiological condition/status (e.g., including real-time vitals and other physiological data), location (bed assignment, unit assignment), reported diagnosis/pathology, procedures performed/ordered, medications administered, laboratory tests, imaging studies, and so on. The clinical data may also include tracked information reported in real-time regarding the location and status of resources, including staff (e.g., clinicians, technicians, engineers, administrative personnel, etc.), beds (e.g., availability status), medical equipment, medical supplies, and so on.

Figure 2:
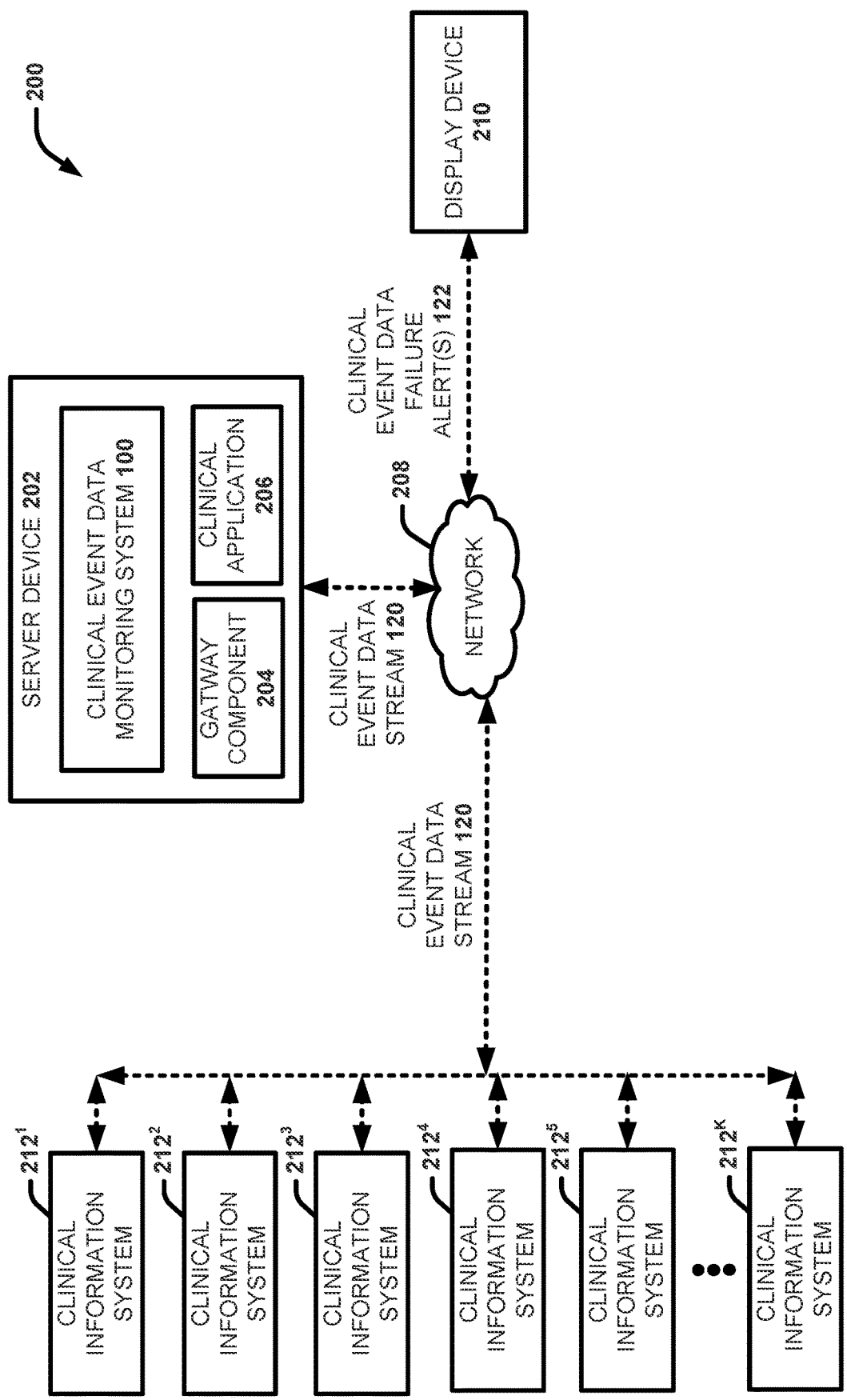
FIG. 2 presents another example, non-limiting system that facilitates online monitoring of clinical data drifts in accordance with one or more embodiments of the disclosed subject matter.

FIG. 2 presents another example, non-limiting system 200 that facilitates online monitoring of clinical data drifts in accordance with one or more embodiments of the disclosed subject matter. System 200 provides an example system architecture in which the clinical event data monitoring system 100 may be implemented. Repetitive description of like elements employed in respective embodiments is omitted for sake of brevity.

In accordance with system 200, the clinical event data monitoring system 200 can be deployed at a centralized sever device 202 that is communicatively coupled to a plurality of different clinical information systems $212^{1-K}$ via a network 208. The network 208 can be a communication network, a wireless network, an internet protocol (IP) network, a voice over IP network, an internet telephony network, a mobile telecommunications network and/or another type of network. The server device 202 can also include a clinical application 206 that corresponds to an application configured to consume the clinical event data included in the clinical event data stream 120 provided by the collective clinical information systems $212^{1-K}$. Additionally, or alternatively, the clinical application 206 can be deployed at a separate system or device (other than the server device 202). System 200 further includes a display device 210 that is also communicatively coupled to the sever device 202 via the network 208. The display device 210 can correspond to any suitable computing device capable of receiving clinical event data failure alerts 122 regarding missing or late clinical events in the clinical event data stream 120 and/or other types of detectable data failure events (e.g., missing or wrong values, improperly formatted data, and others). For example, the display device 210 can correspond to a device used by an operating technician responsible for responding to clinical event data failure alters 122 with remediation actions. Additionally, or alternatively, the clinical event data monitoring system 100 can provide the clinical event data failure alerts 122 via the clinical application 206 (e.g., as in-application alert notifications) on another system/device. In this regard, the display device 210 can be a mobile device, a mobile application for a mobile device, a wall display, a monitor, a computer, a tablet computer, a wearable device, and/or another type of display device.

In some embodiments, the clinical application 206 can also be configured to adjust operating modes or pause operations in response to reception of certain clinical event data failure alerts 122 for certain clinical events. For example, in response to reception of a clinical event data failure alert indicating a particular type of clinical event data used by one version of the clinical application 206 is no longer being received, the clinical application 206 can temporarily employ a different version of the clinical application, (e.g., a different inferencing algorithm using different inputs) capable of operating without the missing data, even though it may be a less efficient or accurate manner of operation. The clinical application 206 can further be configured to switch back to its normal operating mode once the missing clinical event data is received.

The clinical information systems $212^{1-K}$ can correspond to a variety of different electronic information systems and/or devices configured to report, transmit or otherwise provide different types of clinical data for usage by the clinical application 206 or a plurality of different clinical applications. The number of different clinical information systems $212^{1-K}$ can vary. For example, in a hospital environment, multiple information systems typically stream such data through a single gateway which normalizes it into a single data feed. In accordance with system 200, the gateway component 204 can correspond to such a gateway device/component that aggregates the different information feeds provided by the different clinical information systems $212^{1-K}$ and normalizes it into a single data feed of time ordered clinical events. Although the gateway component 204 is located at the server device 202, the particular deployment location of the gateway component 204 can vary, so long as can aggregated the different data feeds prior to reception by the clinical event data monitoring system. In this regard, the clinical event data stream 120 can correspond to a single data feed of time ordered clinical events received from the different clinical information systems $212^{1-K}$.

The clinical information systems $212^{1-K}$ can correspond to a variety of different types of clinical information data systems that provide a variety of different types clinical event data for consumption by the clinical application 206 upon request and/or in automatically in real-time in response to generation and/or reception thereof by the corresponding clinical information system. For example, one or more of the clinical information systems $212^{1-K}$ may include, but are not limited to, one or more patient electronic health record (EHR) systems, one or more patient monitoring systems/devices, one or more bed management systems, one or more medical imaging systems, one or more laboratory systems, one or more facility operations tracking system, one or more medication management systems, one or more admission/discharge recording system, one or more clinical ordering systems, one or more clinical billing systems, and various other electronic medical facility information sources/systems.

The patient EHR system(s) can provide a variety of patient information regarding their medical history, the current reported diagnosis/condition, and clinical notes/reports as well as demographic information for the respective patients that flow through the medical facility. The patient monitoring systems/devices may include various devices and/or systems that track and provide real-time information regarding the current location of the patients, the events and conditions that occur throughout the patient's journey, the clinical status of the patient's, the physiological status of the patients (e.g., vitals) and so on. The bed management system can provide patient flow information regarding current bed placement locations (e.g., inpatient units and/or specific beds) of patients and pending placement requests for beds. For instance, in some implementations, the bed management system can include a system that aggregates and manages all bed requests for the medical facility, including bed requests of different types and/or bed requests associated with different medical units throughout the healthcare facility. In association with managing placement requests, the bed management system(s) can provide a variety of information associated with the patient placement requests. For example, the placement requests can be associated with information regarding details of the requests, such as but not limited to: the type of bed and medical service associated with the request, one or more preferred destination medical units for fulfilling the request, an order type associated with the request, priority information defined for the request, assignment urgency information associated with the request, a type of room requested, event information regarding what triggered the request, clinician instructions regarding specific care instructions for the patient, and the like. The bed management systems can also provide information identifying timing of reception of respective placement requests. current status of the respective requests (e.g., pending, fulfilled, on-hold, etc.), total number of pending requests at the healthcare facility, total number of pending requests per unit, number of pending requests clustered by request type, and the like.

The medical imaging system(s) can provide medical image data and associated reports generated for the respective patients that flow through the medical facility. For example, the clinical event data stream 120 can include information reported by the imaging systems identifying timing of a medical image study conducted and the radiologist report for the study, the actual image data and so on. Similarly, the laboratory system can provide medical laboratory data and associated reports generated for the respective patients that flow through the medical facility. For example, the clinical even data stream 120 can include information reported by the laboratory system identifying lab orders, lab results and so one, reported in real-time. The facility operations tracking system(s) can generate and provide clinical event data regarding various dynamic operational conditions of the medical facility, such as locations and status of resources (e.g., staff, medical supplies and equipment), patient flow data, occupancy levels and so on.

It should be appreciated that the various types of clinical information systems describe above are merely exemplary and other or alternative types of healthcare related data sources/system are envisioned that may provide clinical event data to be included in the clinical event data stream 120.

As described herein, a real-time computer system can be defined a computer system that performs its functions and responds to external, asynchronous events within a defined, predictable (or deterministic) amount of time. A real-time computer system such as system 100, system 200 and other system described herein typically controls a process (e.g., monitoring and detecting clinical data failures) by recognizing and responding to discrete events within predictable time intervals, and by processing and storing large amounts of data acquired from the controlled system (e.g., the clinical event data stream 120). Response time and data throughput requirements can depend on the specific real-time application, data acquisition and critical nature of the type of decision support provided. In the regard, the term "real-time" as used herein with reference to processing and generating information by the respective clinical information systems $212^{1-K}$ refers to performance of these actions within a defined or predictable amount of time (e.g., a few seconds, less than 10 seconds, less than a minute, etc.) between generation of the information by a device or machine (e.g., a biometric sensor, camera, a microphone, etc. or the like), and/or reception of the information by a device or machine (e.g., in response to manual data entry). Likewise, the term real-time as used with reference to reception of the clinical event data stream 120 refers to reception of the clinical event data stream 120 from the one or more of the clinical information systems $212^{1-K}$ within a defined or predictable amount of time (e.g., a few seconds, less than 10 seconds, less than a minute, etc.) after the corresponding information is generated by and/or received by the one or more healthcare systems/sources.

With reference to FIGS. 1-2, regardless of the type of information to be reported in the clinical event data stream 120 and the manner in which the consuming application or system is adapted to use the information, the efficacy and accuracy of the consuming application is dependent on the integrity of the data pipeline. Unfortunately, the information systems reporting the data may suffer intermittent, unexpected, failures due electricity or network outages, equipment malfunctions or software bugs. As a result, some or parts of the data needed by the consuming application or system may be missing or late. In addition, some or parts of the data may be formatted incorrectly for processing by the consuming application/system due to equipment malfunctions, software changes/bugs or data entry errors. Similarly, some or parts of the data may include missing values or incorrect values due to data entry errors and/or device malfunctions (e.g., a device producing erroneous data values, a clinician mixing patient charts, etc.).

The clinical event data monitoring system 100 can facilitate automatically detecting these issues and generating alerts regarding the detected issues in real-time so that the operations engineers can be promptly notified and remediation activities can be promptly initiated. To facilitate this end, the model development component 104 employs principles of machine learning to initially learn "what" the clinical event data stream 120 should include and "when" specific types of the data should be reported under assumed normal operating conditions (without errors or failures associated with data ingestion pipeline). As described in greater detail below, in various embodiments, the model development component 104 can further generate one or more parametric and/or non-parametric models (e.g., TTE models $112_{1-N}$) for the clinical data stream 120 based on this learned information that can facilitate detecting missing or late data as well as other data failure events. The other data failure events can include, but are not limited to, data format errors, missing data values, and incorrect data values. The detection component 106 can further employ these models (e.g., TTE models $112_{1-N}$) in an online or runtime environment in association with monitoring a live clinical event data stream 120 being transmitted to a consuming application/system to detect one or more of these data failure events. The alert component 114 can further generate and provide corresponding clinical event data failure alerts 122 in response to detection of the one or more data failure events. In this regard the clinical event data failure alerts can 122 can include (but is not limited to), information identifying a detected data failure event, the timing of the detected data failure event, the type of the detected data failure event (e.g., missing data, late data, format error, missing value error, incorrect value error, etc.), information regarding the type of data associated with the data failure event (e.g., the specific clinical event type that was missing or late, the improper/missing value, etc.), and originating source of the data (e.g., the information system/device that reported or should have reported the data). The alert component 114 can provide the clinical even data failure alerts 122 to one or more defined entities using one or more electronic notification mechanisms. For example, the alerted component 114 can provide the alerts as in-application notifications (e.g., withing the clinical application 206 that consumes the clinical event data stream 120), to a control command center/system, to a display device employed by an operating technician, or the like.

To facilitate this end, the system 100 defines the specific pieces of data that clinical event data stream 120 should include as clinical events. The number of different clinical events monitored can vary and will be based on the level of granularity used to define the different clinical events. For example, assume the clinical data stream 120 includes medication administration information for all patients in hospital that identifies the specific medication administered (e.g., by a medication code), the patient to which it was administered, the dose, and the timing of administration. Such medication information may be generated and reported in the clinical event data stream 120 by various types of electronic reporting systems at the hospital in real-time (e.g., in response to manual entry into an electronic medication reporting system, directly from the medication administering device, captured and reported via image analysis technology, etc.). According to this example, the system may define reception of any reported medication administration, regardless of the specific medication administered, the patient or the dose as type of clinical event. Alternatively, the system 100 may define a separate clinical event for each specific medication such that an administration of medication A is considered a distinct clinical event, administration of medication B is considered another distinct clinical event, administration of medication C is considered another distinct type of clinical event, and so on. Still in yet another example, the system may define distinct clinical events that differ with respect to one of medication type, patient, or dose.

In this regard, the level of granularity used to define the clinical events, that is the distinct contents of the a data object or data string that constitute a clinical event, will vary depending on the manner in which the data is used by the consuming application/system and the architecture of the information system generation pipeline from which the clinical event data stream 120 is received (e.g., the number, type and configuration of the information sources reporting the information included in the clinical event data stream 120). In the case of predicting missing clinical data, it is important to understand what the root causes of such missing data might be when defining the specific clinical events to be monitored in the clinical event data stream 120. In most cases missing data are due to some infrastructure problem, such as a server being down, a network malfunction and so on. In such cases many events which use the same system are going to become missing. To give a concrete example, assume that analysis system in the lab suffers from a malfunction, all labs request to that system will go missing. This means that instead of monitoring all of the potentially different events types that may the proposed lab system may report, the system 120 can cluster all event types which arrive from a specific source and monitor just the cluster representatives. Thus, in some embodiments, the system 100 can define distinct clinical events based on the source providing the clinical data, wherein all data coming from one source corresponds to one event type.

Additionally, or alternatively, the system 100 can take the different clinical events from a defined clinical ontology such as the UMLS or a similar clinical ontology. A clinical ontology aims to arrange medical knowledge in a large graph structure where nodes hold medical terms, and connecting edges define the relation between nodes. In the UMLS and other ontologies, the most common relation is the abstraction relation, also referred to as an is-a relation. In an abstraction relation, general concepts point to more specific concepts. Thus, in some embodiments, the system 100 can employ the different nodes corresponding to more general clinical concepts in a defined clinical ontology as the different clinical events to be monitored and cluster all clinical events that fall under each node as belonging to the same type of clinical event. For example, assume a higher-level node in the ontology corresponds to vital signs and lower-level nodes connecting that node correspond to specific types of vital signs, such as blood pressure, heart rate, pulse, temperature and oxygen saturation. The system can define all reported vital signs in the clinical event data stream as one type of clinical event. Additional techniques for determining the best level of abstraction for defining the distinct clinical events to be monitored in the clinical event data stream 120 are discussed in greater detail infra with reference to FIG. 6.

Regardless as to how the different clinical events to be monitored in the clinical event data stream 120 are defined, once they are defined, the system 100 can assign each distinct clinical event a unique event identifier. In some embodiments, the system 100 can use existing medical terms or medical codes used by the information system/source providing the clinical data to identify different types of clinical event data, such as existing procedure codes, medication codes, and the like. In other embodiments, the system 100 can generate unique identifiers for the different types of clinical events. For purposes of this disclosure, each defined clinical event can be referred to as one event type. Information defining the different clinical event types to be monitored can be stored in memory 116, the model database 110, or another suitable data structure accessible to the clinical event data monitoring system. The information defining the different clinical event types can for example, include a unique event identifier (ID) for each different clinical event and information describing the characteristics/requirements of the data belonging to each event type. For example, the information describing the characteristics/requirements of the data belonging to each event type can include (but is not limited to), the information system/source from of the data corresponding to each clinical event type, the contents of the data, metadata tags used to identify the data included in each event type, formatting requirements for the data, expected values for the data, and any other machine readable and/or natural language information describing the data belonging to each event type.

In one or more embodiments, to predict when events are likely to be missing, all reported clinical events included in the clinical event data stream 120 can be time-stamped with information identifying their timing of reception by the system 100, and the model development component 104 can model their expected arrival times in a time-to-event (TTE) model that estimates the expected arrival times between two events of the same type. For example, the reception component 102 can receive the clinical data stream 120 in real-time and generate a time stamp for each identified clinical event marking its timing of reception. The model development component 104 can generate a separate TTE model for each different event type. With these embodiments, the TTE models $112_{1-N}$ in the model database 110 can respectively correspond to the different TTE models for the different event types. The model development component 104 can initially train the respective TTE models $112_{1-N}$ models in a training and development phase (offline). Once trained, the detection component 106 can apply the respective TTE models $112_{1-N}$ in an online phase (e.g., in live or in real-time) to a live clinical event data stream 120 (e.g., as it is received in real-time) to detect missing or late clinical events.

During the training phase the system 100 collects the arrival times for all the defined events to be monitored. For example, to generate the training data, the reception component 102 can record the clinical event data stream 120 as it is received over time and time stamp all identified clinical events included in the recorded data stream with their arrival times. In this regard, the training data can include previously (past) recorded clinical event data stream 120 data for the particular hospital system (or similar system) to be monitored. The recorded clinical event data stream data 120 can be stored in memory 116, the model database 110 and/or in another suitable data structure accessible to the model development component 104. In some embodiments, the training data can also be supplemented with previously recorded clinical event data stream data 120 from similar systems (e.g., other hospital systems for instance that can be used as references). When enough training data has been collected to form robust statistics, the model development component 104 can fit (i.e., train) a TTE model 112 for each event type. The amount of training data that constitutes "enough" for each event type can vary and can be predefined as function of the number input sample, wherein each input sample corresponds to a received event with its recorded arrival time. For example, in some implementations, the training data can reflect clinical event data steam 120 data recorded over a past week, two weeks, month, etc., or as little or a long as needed to obtain enough reported instances of each defined clinical event type to be modeled. The model development component 104 can further regularly re-train and tune the models over time as new clinical event data stream 120 data is received and recorded by the system 100.

Figure 3:
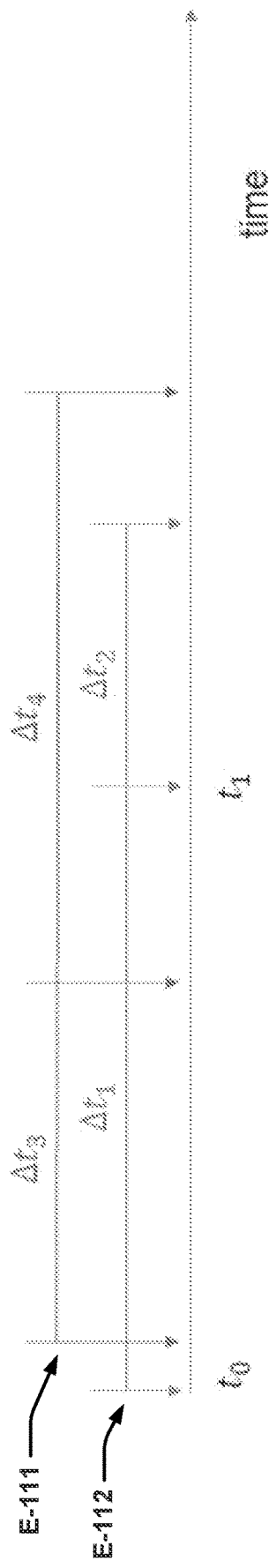
FIG. 3 illustrates modeling expected event arrival times using a time-to-event model in accordance with one or more embodiments of the disclosed subject matter.

FIG. 3 illustrates modeling expected event arrival times using a time-to-event model in accordance with one or more embodiments of the disclosed subject matter. With reference to FIGS. 1-3, in the embodiment shown in FIG. 3, E-111 corresponds to a first defined clinical event type and E-112 corresponds to a second defined clinical event type. Assume for example, the clinical event data stream 120 correspond to clinical event data reported by a variety of disparate information systems associated with a complex hospital system that serves a large number of patients. In this context, assume the upper line E-111 corresponds to a reported white blood cell count for any patient in the hospital and the lower line E-112 correspond to a reported blood pressure for any patient. In association with reception of the clinical event data stream 120, the reception component 102 records the time between consecutive arrivals of the same event types. In the example shown in FIG. 3, each downward pointing vertical arrow correspond to an instance of a received event which is recorded as a function of their arrival times. For each event type, all its occurrences are recorded and the related time differences are computed (e.g., manually, via the model development component 104, and/or via the reception component). For example, in FIG. 3, $\Delta t_1$ represents the time difference between arrivals of the first and second instances of event type E-112 and $\Delta t_2$ represents the time difference between arrivals of the second and third instances of event type E-112. Likewise, $\Delta t_3$ represents the time difference between arrivals of the first and second instances of event type E-111 and $\Delta t_4$ represents the time difference between arrivals of the second and third instances of event type E-111. In accordance with the example shown in FIG. 3, the occurrences of each event type are recorded for all patients in the hospital. It should be appreciated however that the events may be grouped into sub-groups by various factors, such as by ward or department, patient diagnosis/pathology, patient demographic factors, or another factor, and the model development component 104 can generate separate TTE models for each sub-group. For instance, as each ward in the hospital has different set of patients and treatments, the model development component can parametrize each TTE model independently per ward. For brevity of the following description, the ward designation is omitted.

In accordance with these embodiments, the training data for each TTE model $112_{1-N}$ thus includes a sequence of time differences $\Delta t_i$ per event type. Using this training data, the model development component 104 can train the respective TTE models $112_{1-N}$ to estimate the probability that an observed time difference between the last occurrence of each event is expected using the training data and using one or more machine learning techniques. In this regard, the respective TTE models $112_{1-N}$ can incorporate one or more machine learning models. The type machine learning models used for the respective TTE models $112_{1-N}$ can vary. For example, the respective TTE models $112_{1-N}$ can employ various types of machine algorithms, including (but not limited to): deep learning models, neural network models, deep neural network models (DNNs), convolutional neural network models (CNNs), generative adversarial neural network models (GANs), long short-term memory models (LSTMs), attention-based models, transformers, or a combination thereof. In some embodiments, the respective TTE models $112_{1-N}$ can additionally or alternatively employ a statistical-based model, a structural based model, a template matching model, a fuzzy model or a hybrid, a nearest neighbor model, a naïve Bayes model, a decision tree model, a linear regression model, a k-means clustering model, an association rules model, a q-learning model, a temporal difference model, or a combination thereof. The model development component 104 can employ supervised, semi-supervised and/or unsupervised training methods for training the respective TTE models $112_{1-N}$ based on the collected training data.

In one or more embodiments, each of the TTE models $112_{1-N}$ can incorporate one or more statistical distribution models and a survival analysis function. The survival analysis function comprises a machine learning function that has been used to determine the probability that a patient, device, or other object of interest will survive beyond any specified time. In this case, the model development component 104 applies the survival analysis function to determine the likelihood that an associated event time difference is at least of that long (i.e., expected), as estimated based on the probability distribution of the sequence of time differences $\Delta t_i$ per event represented in the training data.

In this regard, the sequence of time differences $\Delta t_i$ per event type represent a random process that can be modeled using a probability distribution. The model development component 104 can model the probability distribution of time differences for each event using parametric and/or non-parametric statistical models (and/or other machine learning models). In one or more embodiments, the model development component 104 can model the probability distribution of time differences per event type using a Weibull distribution. A Weibull distribution is a parametric family of probability distributions typically applied in the fields of mechanical reliability and survival analysis.

Figure 4A:
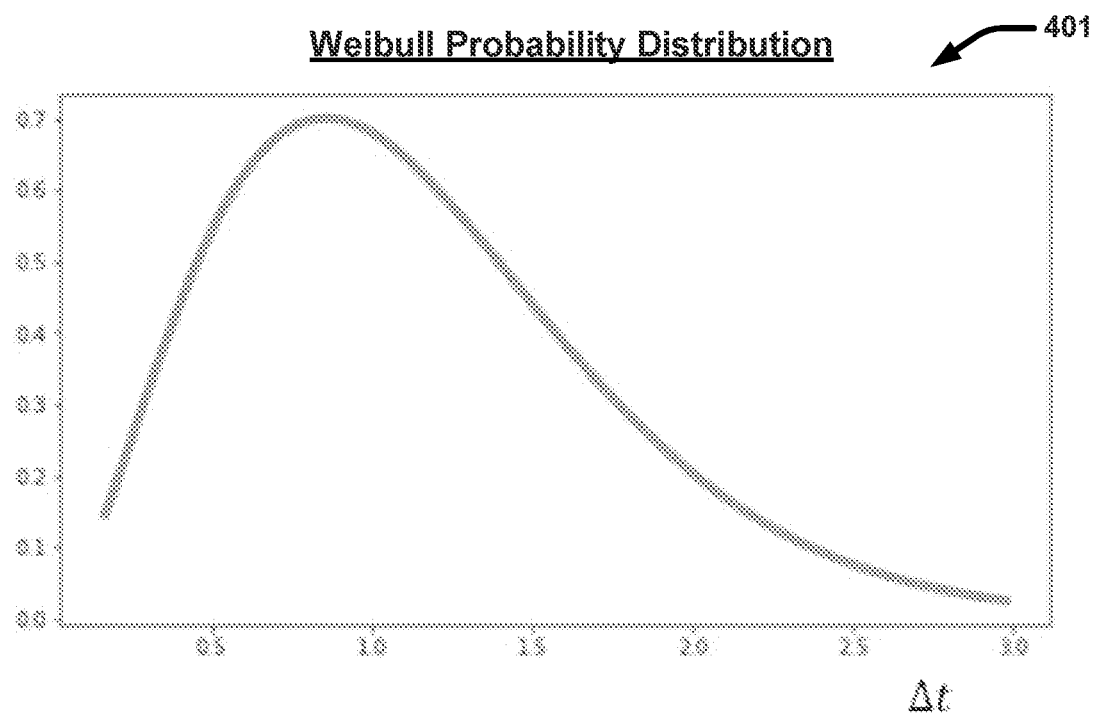
FIGS. 4A-4B illustrate an example Weibull probability distribution and its associated survival function in accordance with one or more embodiments of the disclosed subject matter.
Figure 4B:
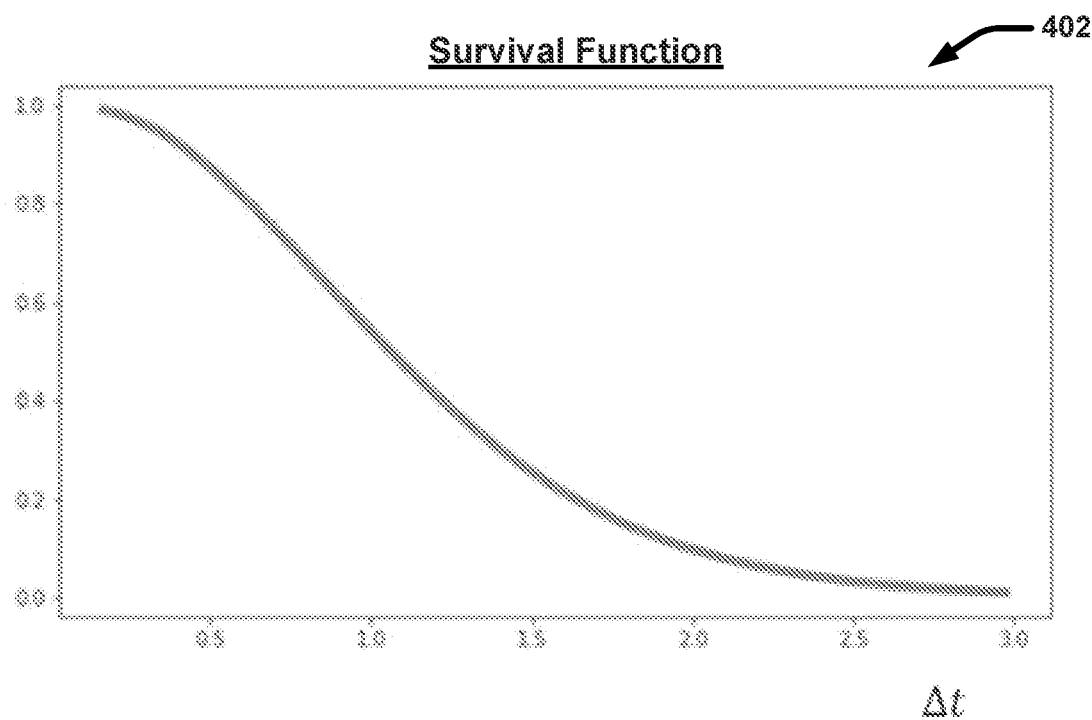

FIGS. 4A-4B illustrate an example Weibull probability distribution 401 and its associated survival function 402 in accordance with one or more embodiments of the disclosed subject matter. For both the Weibull probability distribution 401 and its associated survival function 402, the x-axis represents the distribution of time differences Δt, and the y-axis represents the probability associated with occurrence of the respective time differences.

With reference to FIGS. 1-4B, in various embodiments, the model development component 104 can model each events arrival time differences a Weibull probability distribution 401 and learn its parameters. The model development component 104 can further compute a survival analysis function 402 using the Weibull probability distribution to estimate the expected time between arrival of a next event of the same type. With these embodiments, the survival function (SF) for the Weibull distribution corresponds to Equation 1, where λ is a scale parameter and κ a shape parameter:

$$SF(x \mid \lambda, \kappa) = e^{-(\frac{x}{\lambda})^{\kappa}}. \quad \text{Equation 1}$$

In accordance with these embodiments, the system can also set additional parameters for the Weibull probability distribution. These additional parameters can include the number of samples required to get sufficient accuracy (N), the minimal and maximal time for collecting samples ($T_0$ and $T_1$ respectively), and the test time window T_t. After the training component 104 has modeled the probability distribution of time differences per event type using the Weibull probability distributions or another non-parametric probability distribution based on the training data, the detection component 106 can employ the respective probability distributions and the survival function to estimate whether an observed time difference between the last occurrence of a particular event time is expected during the online phase. In particular, during the online phase the reception component 102 an receive the clinical event data stream 120 in real-time and record the arrival times for all defined clinical event types as they are received. The detection component 106 can further compute the observed time difference between the last occurrence of each monitored event every predefined time interval and apply the corresponding TTE model $112_{1-N}$ for each event to estimate whether the observed time difference is expected. For example, the predefined time interval may be once every N minutes, wherein N can vary (e.g., once every minute, once every 5 minutes, once every 30 minutes, once every 60 minutes, etc.). In this regard, application of the correspond TTE model $112_{1-N}$ for each monitored event can comprise computing the survival function for each event using the corresponding TTE model $112_{1-N}$, which corresponds to a probability distribution of the expected time differences between events of the same type. The output of the survival function comprises a probability value that the observed time difference is expected. The system 100 can further define a threshold acceptable probability value, wherein observed time differences for events that fall below the threshold are considered missing event candidates.

In some embodiments, the alert component 114 can be configured to generate a clinical event data failure alert 122 for all detected missing event candidates. In other embodiments, the detection component 106 can be configured to track the number of missing event candidates detected for each event type over time, and the alert component 114 can be configured to generate a clinical event data failure alert in response to the number of missing event candidates for a specific event type exceeding a threshold count value. This threshold count value can further be restricted as a function of a defined time interval. For example, the detection component 106 can be configured to sum the number of missing event candidates detected every M minutes (e.g., every 10 minutes, every 30 minutes, every 60 minutes and so on) and the alert component 114 can be configured to generate a clinical event data failure alert in response to the summed candidates exceeding the threshold count value for that time interval. In this regard, as expressed mathematically in terms of the survival function, assume the threshold acceptability value for the survival function is $T_0$, and the count threshold for the time interval is $T_1$. In some implementations, if the value of the survival function is below $T_0$, then the detection component 106 can raise the count of missing event candidates by 1, and if the value of the survival function is greater than or equal to $T_0$, than the detection component can lower the count by 1, as expressed in Equation 2.

$$\text{Missing Event Candidate} = \begin{cases} 1 \mid SF(x) < T_0 \\ -1 \mid \text{otherwise} \end{cases}. \quad \text{Equation 2}$$

The alert component 114 can further generate a corresponding clinical event data failure alert for the event when the summed missing event candidate counter exceeds $T_1$. An alternative scheme could sum all missing data candidate values so that the system can react faster to large scale data drops, such a scheme is also less prone to false alarms at the cost of lesser reporting granularity.

Additionally, or alternatively, the detection component 106 can incorporate a mechanism that accounts for the severity (i.e. duration) of the time differences between consecutive arrivals (or failures thereof) of events of the same type over time. With these embodiments, the detection component 106 can aggregate the probabilities for defined clinical events of the same type over sequential time intervals of the predefined time interval, and the alert component 114 can generate missing data failure alerts based on the aggregated probabilities for a same event exceeding a threshold value. In particular, since the survival function is a monotonically decreasing function its value conveys information on the severity of the delay. Thus in some embodiments, instead of counting the number of times a TTE model estimated survival function value down-crosses the threshold survival function value, the detection component 106 can sum the value of this function over time. For example, because the survival function value is close to zero and with small dynamic range, the detection component 106 can take the negative logarithm of the survival function and normalize it such that it has a value of 1 when it crosses the threshold and set a defined upper limit value (e.g., of 10 or another value) to this function. The alert component 114 can further generate a missing event alert for the corresponding TTE model in response to the value of the survival function reaching or exceeding the upper limit value. By using this scheme, the detection component 106 and the alert component 114 incorporate a mechanism which weights the length of delay. In this way, the detection component 106 pushes the scheme to become more concerned as the delays get longer over time.

Figure 5:
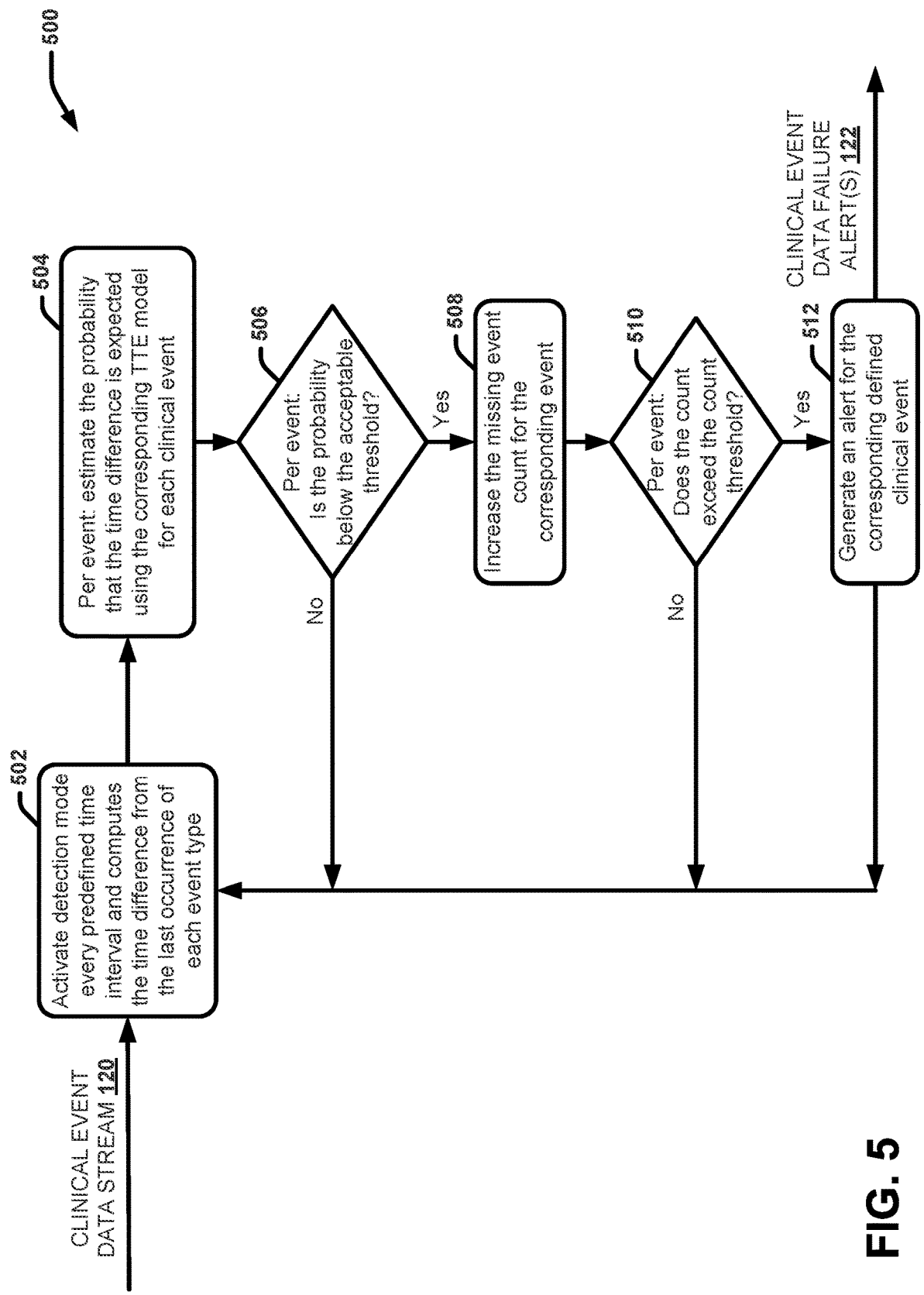
FIG. 5 illustrates a high-level flow diagram of an example process for detecting clinical data drifts in accordance with one or more embodiments of the disclosed subject matter.

FIG. 5 illustrates a high-level flow diagram of an example process 500 for detecting clinical data drifts in accordance with one or more embodiments of the disclosed subject matter. Process 500 provides an example process that can be performed by the clinical event data monitoring system 100 in an online environment using the detection component 106 to monitor a live clinical event data stream 120 as it is received over time and detect missing or late events and other data failure events. In this regard, process 500 illustrates a continuous process that can be repeated indefinitely. Process 500 assumes the clinical event data monitoring system 100 receives the clinical event data stream 120 in real-time and records the arrival times of all defined clinical events that are received within the data stream. Process 500 further relies on the specific clinical events to be monitored being previously defined and previously generated TTE models $\mathbf{112}^{1\text{-}N}$ for each of the defined clinical events.

In accordance with process 500, at 502, the system activates detection mode every predefined time interval and computes the time difference from the last occurrence of each event type (e.g., via the detection component 106). For example, the predefined time interval may be every minute, every 5 minutes, every 10 minutes, every 30 minutes, every 60 minutes and so on. For example, the reception component 102 can record the arrival times of all received clinical events of the defined clinical events and the system can maintain a running list of received time-ordered events with their arrival times for each defined clinical event of the same type. In this regard, the system records the times between consecutive arrivals of events of the same type. The system can further track those events which have not been received. Every predefined time interval, the detection component 106 can examine the running list to identify the last (e.g., most recent) arrival time for each of the defined clinical events and calculate the difference between the current time and the last arrival time. For those events which have not been received at least once, the detection component 106 can apply a default time difference computed as function of the current time and a predefined past point in time. For example, the predefined past point in time can correspond to the point in time when the system began monitoring all events (e.g., time t_0). In other implementations, the predefined past point in time can reset back to zero every predefined time frame (e.g., every 24 hours, every 48 hours, etc.).

At 504, per each event type, the detection component 106 can estimate the probability that the last time difference is expected using the corresponding TTE model (of the TTE models $\mathbf{112}^{1\text{-}N}$) for each of the defined clinical events. In this regard, the input to each TTE model 112 includes the current time difference from the last occurrence of the same event type, and the output of the TTE model comprises the estimated probability that the time difference is expected. In embodiments in which the TTE models employ a survival analysis function modeled on historical time differences between consecutive arrivals of same event types, at 504, the system can compute the value of the survival analysis function for each of the defined clinical events based on the current time differences. With these embodiments, the estimated probabilities that the time differences are expected will be expressed as a survival function value. As described above, the detection component 106 can use parametric (e.g., a Weibull distribution function) and non-parametric (e.g., a Parzen windows probability estimation) statistical models of the probability distributions of the historical time differences for each of the defined clinical events to compute the survival function. In some implementations, the TTE models can also be configured to evaluate additional input parameters, such as but not limited to, the particular hospital ward or department associated with the event, patient related parameters (e.g., patient subgroups defined based on demographic factors, diagnosis/pathology factors, and others), contextual factors (e.g., time of day, day of week, etc.), and other factors.

At 506, per each event type, the system determines whether the probability that the time difference is expected below the acceptable threshold. For example, in implementations in which the probability is expressed as a survival function value, the detection component 106 can determine whether the survival function value is less than threshold survival function value. If the probability is above the threshold at 506, than the detection component 106 assumes the corresponding defined clinical event is not late or missing and waits to revaluate the same clinical event upon the next activation of the detection mode at 502 upon passing of the next predefined time interval. In some implementations, the detection component 106 may also lower the missing event candidate count for that event by one as well. If however at 506 the probability is below the threshold, than at 508, the detection component increasing the missing event count for the corresponding event by one.

At 510, the detection component 106 further examines the missing event candidate count for each of the defined events and determines whether the count exceeds the count threshold. In particular, the detection component 106 can aggregate (e.g., add or sum) the missing event candidates detected for each event type over a predefined time frame (e.g., every 10 minutes, every 30 minutes, every 60 minutes, every 24 hours, etc.) and determine whether the aggregated count exceeds the threshold within the predefined time frame. The detection component 106 can further reset the count back to zero every predefined time frame. The count threshold can vary for different clinical events or the same count threshold can be used for all clinical events. If at 510, the detection component 106 determines that the count for a clinical event type does not exceed the threshold count, then detection component 106 waits to revaluate the same clinical event upon the next activation of the detection mode at 502 upon passing of the next predefined time interval. However, if at 510 the detection component 106 determines that the count for a clinical event type exceed the threshold count, then at 512, the alert component 512 generates a clinical event data failure alert 122 for the corresponding defined clinical event. For example, the alert can comprise information identifying the defined clinical event and indicating the defined clinical event data is not being received (i.e., missing or late enough to be considered missing) due to some upstream failure. The alert component 512 can further provide the data failure alert to one or more defined entities in real-time (e.g., in response to generation thereof) using one or more electronic notification mechanisms. For example, the one or more defined entities can include a clinical application configured to receive and consume the event data included in the clinical event data stream, an operating technician responsible for managing the operations of the clinical application (e.g., via a device/application associated with the operating technician), or the like.

Figure 6:
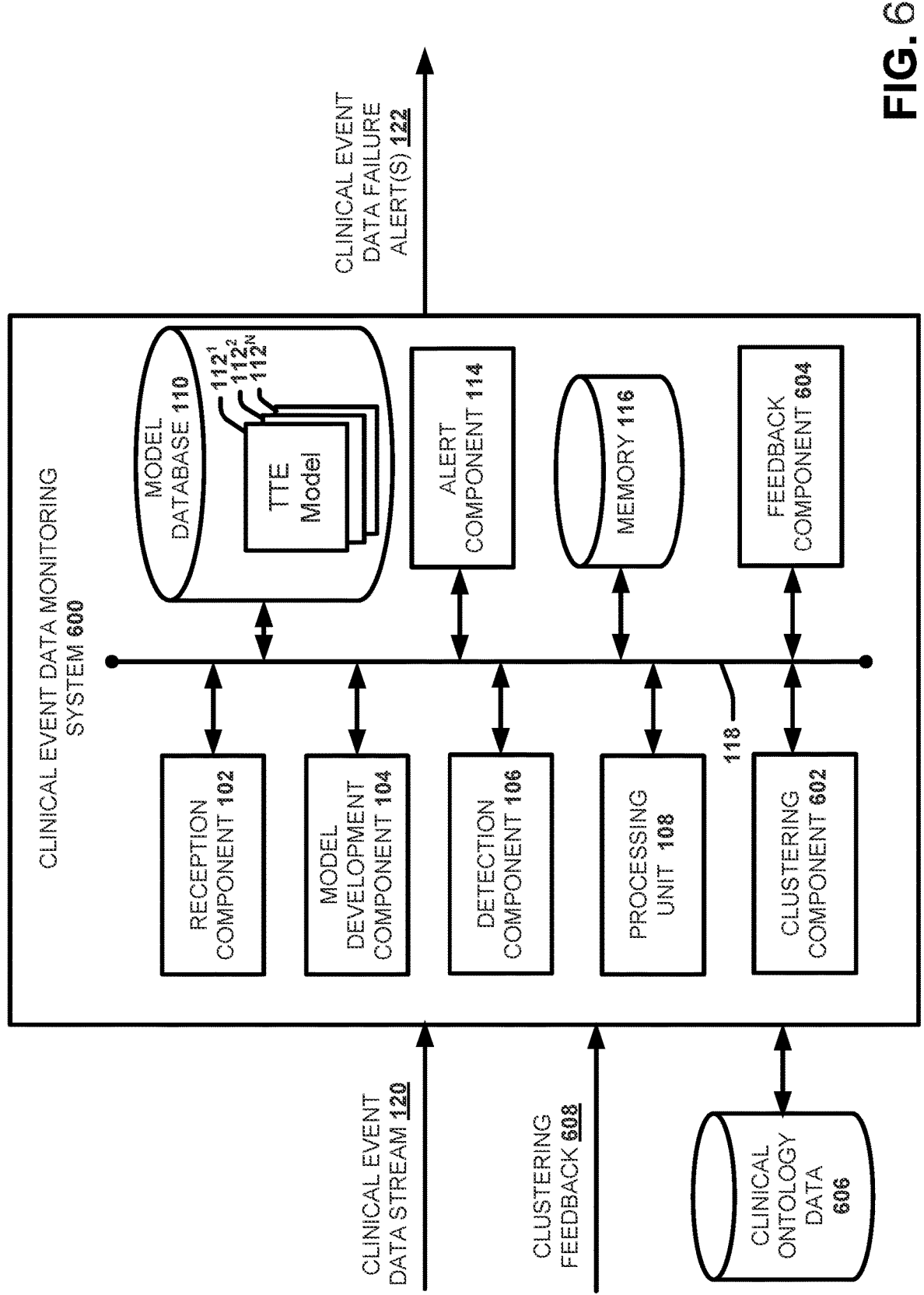
FIG. 6 illustrates a block diagram of another example, non-limiting system that facilitates online monitoring of clinical data drifts in accordance with one or more embodiments of the disclosed subject matter.

FIG. 6 illustrates a block diagram of another example, non-limiting clinical event data monitoring system 600 that facilitates online monitoring of clinical data drifts in accordance with one or more embodiments of the disclosed subject matter. System 600 includes same or similar components as system 100 with the addition of clustering component 602, feedback component 604, clinical ontology data 606 and clustering feedback 608. Repetitive description of like elements employed in respective embodiments is omitted for sake of brevity.

One of the main challenges associated with the proposed techniques for automatically detecting missing or late clinical events in the clinical event data stream is determining the proper level of abstraction for defining the specific clinical event types to be monitored. For example, some of the events may be rarely witnessed while other may be received at a high frequency. Detecting missing events in the face of rarity poses a significant challenge. Some of the events are truly rare, a rare treatment to a rare disease, while others may seem so due to interchangeability in medical treatment (e.g., two pain medications with same the active ingredient and different commercial designations). With this problem in mind the clinical event data monitoring system 600 provide several mechanisms facilitated by the clustering component 602, the feedback component 604, and defined clinical ontology data 606 to automatically and semi-automatically determine define the different clinical events to be monitored.

In one or more embodiments, the clustering component 602 can cluster related type of clinical data together as a single event type to be monitored. With these embodiments, all data items belonging to the same cluster can be treated as the same type of clinical event and model development component 104 can generate and apply the same TTE model for all events belonging to the same cluster. In some embodiments, the clustering component 602 can cluster related events together based on the clinical information system/source that provides the data. For example, with reference again to FIG. 2, the clinical event data stream 120 can correspond to a single stream of data aggregated from a plurality of different clinical information system $112^{1-K}$. In some implementations of these embodiments, the clustering component 602 can cluster all types of data coming from the same clinical information system as the same type of clinical event. This means that instead of monitoring all potential different event types, the detection component 106 can cluster all event types which arrive from a specific information system and monitor just the cluster representatives.

The feedback component 604 can further provide a manual clustering tool that allows one or more users (e.g., operating engineers or the like) to manually tell the system 600 which events types to group together. With these embodiments, the feedback component 604 can provide for receiving clustering feedback 608 from users identifying clustering criteria for grouping related types of clinical data together as the same type of clinical event. The clustering component 602 can further defined the different clinical event types based on the received clustering criteria.

Additionally, or alternatively, the clustering component 602 can employ defined clinical ontology data 606 to automatically and/or semi-automatically cluster related clinical concepts or terms as belonging to same types of clinical events. The clinical ontology data 606 can correspond to a defined clinical ontology (e.g., UMLS or the like) that arranges medical knowledge in a graph structure where nodes hold medical terms, and connecting edges define the relation between nodes. In the UMLS and other ontologies, the most common relation is the abstraction relation, also referred to as an is-a relation. In an abstraction relation, general concepts point to more specific concepts.

Figure 7:
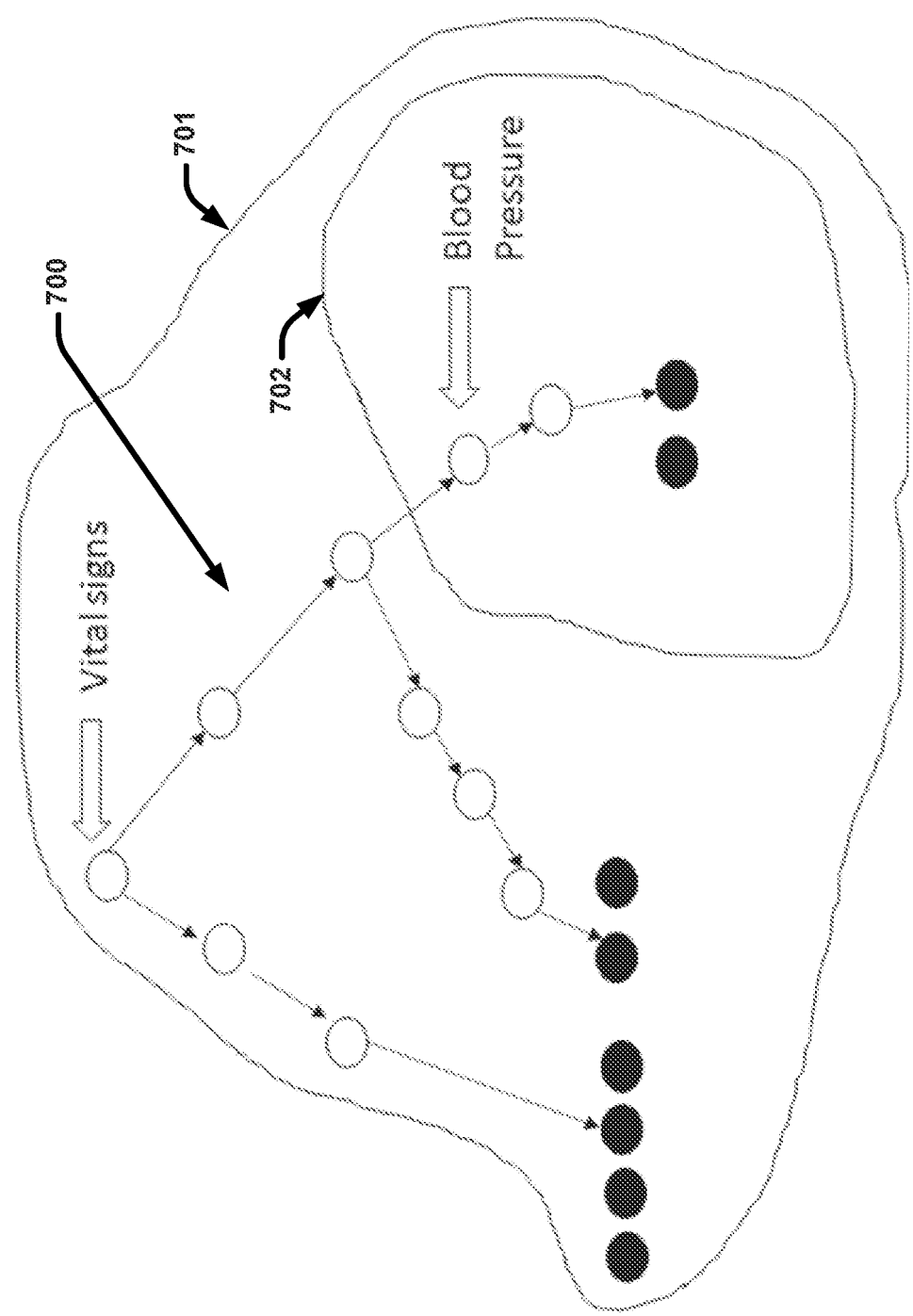
FIG. 7 presents an example clustering scheme for clustering clinical events defined according to a defined clinical ontology in accordance with one or more embodiments of the disclosed subject matter.

FIG. 7 presents an example clinical ontology graph structure 700 and an example clustering scheme for clustering clinical events based on the clinical ontology graph structure in accordance with one or more embodiments of the disclosed subject matter. The clinical ontology graph structure 700 corresponds to a small portion of a larger clinical ontology graph structure that stems from an internal root node corresponding to vital signs. In this example, the graph structure comprises a plurality of different nodes respectively represented by the circles that correspond to clinical terms or concepts related to vital signs. The arrowed lines between the nodes indicate the relationships between the clinical terms or concepts. The white circles correspond to internal nodes (higher level nodes) and the black circles correspond to descendent nodes.

With reference to FIGS. 6 and 7, in some embodiments, the clustering component 602 can employ the root nodes corresponding to the more general clinical concepts (e.g., internal nodes and/or root nodes) in the defined clinical ontology data 606 as the different types of clinical events to be monitored and cluster all nodes corresponding to clinical events/terms that fall under each root node as belonging to the same type of clinical event. For example, as illustrated in FIG. 7, the clustering component 602 can cluster all nodes in the graph structure that descend from the root node for vital signs into the same cluster 701. To facilitate this end as applied to a larger more complex graph structure for the entire clinical ontology (or a portion thereof), the clustering component 602 can use the mapping of terms to defined clinical ontology concepts to find the root nodes, find all descendant concepts in the graph, and build the inverse graph to associate descendent nodes to the root nodes. In other words, given a select internal node (e.g., a white node), the clustering component 602 can traverse up the links of the ontology to a proper abstraction level (e.g., to a root node in the ontology), then descend from that inner node to all the reachable terminal nodes (e.g., the black nodes). The clustering component 602 can further define the set of reachable nodes as the cluster, while the internal node is treated as the cluster center. During the training phase, instead of training for each input event, the model development component 104 can fit a TTE model 112 for each cluster. During the online phase, for each input event its cluster identity is identified and the proper model which represents that cluster is queried and applied.

The main difficulty in this graph based clustering scheme is how to define the proper level of abstraction. To this end, the aforementioned manual clustering tool provided by the feedback component 604 can further be used to allow operations engineers to designate an internal node as a cluster center and the clustering component 602 can define all of its descendants as a single cluster. For example, the feedback component 604 can present all or portions of the graph structure for the defined clinical ontology to a user (e.g., an operations engineer or the like) via an interactive graphical user interface. For instance, the graph structure can correspond to a more complex version of graph structure 700 with labels applied to the respective nodes identifying the clinical terms/concepts they represent. The displayed graph structure can be interactive and selectable, allowing the user to select root nodes for generating clusters of clinical events, and/or defining cluster directly by encircling the nodes to be included in a same cluster (or otherwise selecting the nodes to group together into a same cluster). With these embodiments, the clustering feedback 608 can include the user marked root nodes and/or user defined clusters via interaction with the graph structure via the interactive user interface.

Still in other embodiments, the clustering component 602 can utilize concepts that clinicians are querying in association with usage of the clinical application 206 or other clinical applications to define a proper level of abstraction. By focusing on such concepts the system is assured that it is mentoring meaningful concepts. With these embodiments, the clustering feedback 608 can correspond to clinical query terms regularly used by clinicians in association with searching for clinical data items that are expected to be included in the clinical event data stream. The clustering component 602 an further find the nodes in the clinical ontology graph structures corresponding to the query terms and use these nodes a root nodes for generating clusters of related terms. For example, in FIG. 7, assume the term blood pressure was received in a clinical search query. In this example the term blood can be used by the clustering component to resolve several nodes as defined in the ontology and group them together as one event type cluster 702, while the term vital signs was used to resolve a much larger context. During system design the clustering component 602 may be configured to exclude such cases and focus on disjoint clusters so that an event always relates to the lower or higher level of abstraction. Excluding contained clusters reduces the number of tracked clusters at the expense of lower granularity or less robust statistics. In some implementations of these embodiments, the feedback component 604 can also provide a querying tool that allows clinicians to enter the query terms to find and retrieve the corresponding data as stored at the respective clinical information systems $112^{1-K}$ and/or as previously aggregated and stored historical clinical event stream data 120 (e.g., stored in memory 116 or another accessible data structure).

Figure 8:
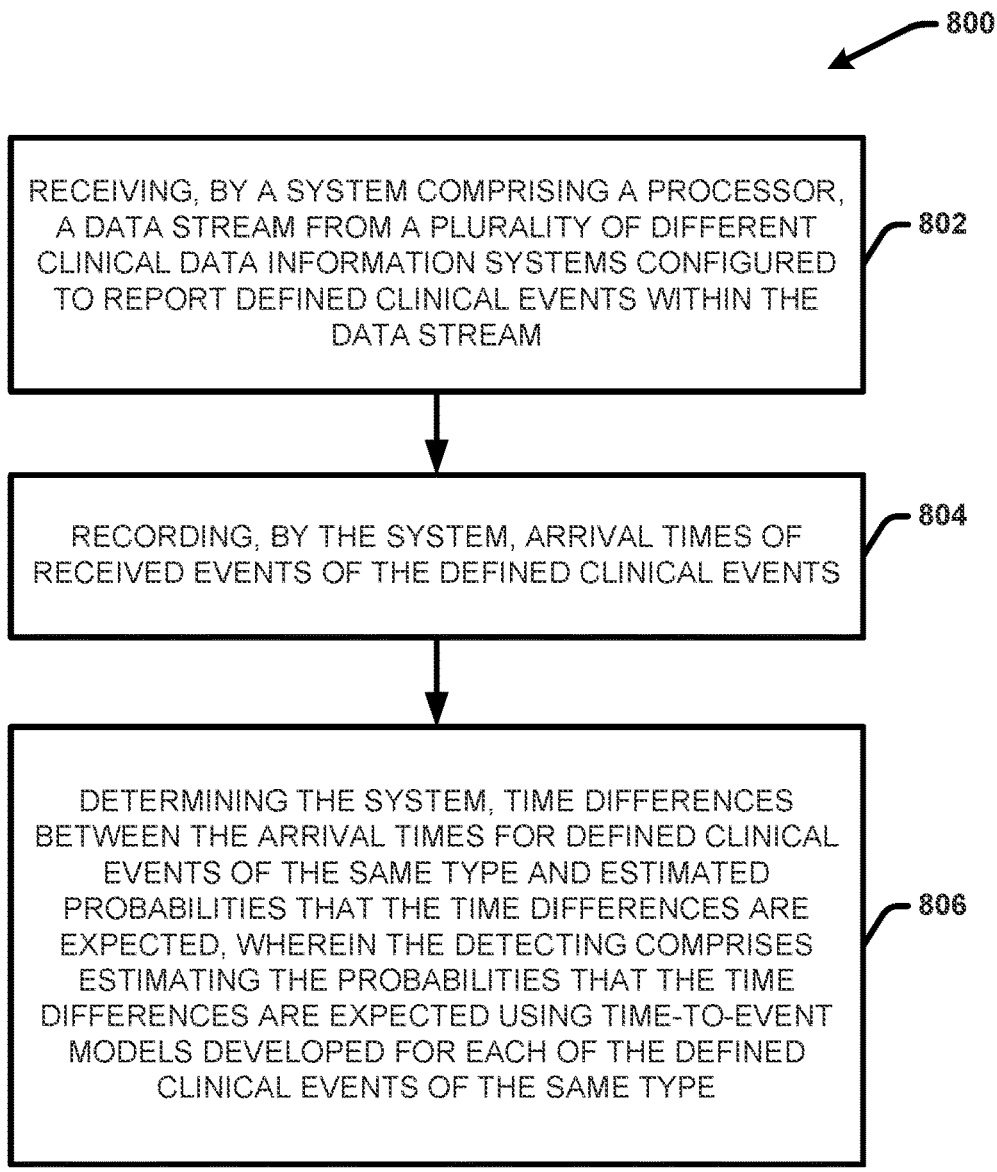
FIG. 8 illustrates a high-level flow diagram of an example computer-implemented method for detecting clinical data drifts in accordance with one or more embodiments of the disclosed subject matter.

FIG. 8 illustrates a high-level flow diagram of an example computer-implemented method 800 for detecting clinical data drifts in accordance with one or more embodiments of the disclosed subject matter. Repetitive description of like elements employed in respective embodiments is omitted for sake of brevity.

In accordance with method 800, at 802, a system operatively coupled to a processor (e.g., system 100, system 200, system 600, or the like) receives comprising a data stream (e.g., clinical event data stream 120) from a plurality of different clinical data information systems (e.g., clinical information systems $212^{1-K}$) configured to report defined clinical events within the data stream (e.g., via reception component 102). At 804, the system records arrival times of received events of the defined clinical events (e.g., via the reception component 102). At 806 the system detects (e.g., via detection component 106) data failure events associated with the data stream based on time differences between the arrival times for defined clinical events of the same type and estimated probabilities that the time differences are expected, wherein the detecting comprises estimating the probabilities that the time differences are expected using time-to-event models (e.g., TTE $112^{1-N}$) developed for each of the defined clinical events of the same type.

Figure 9:
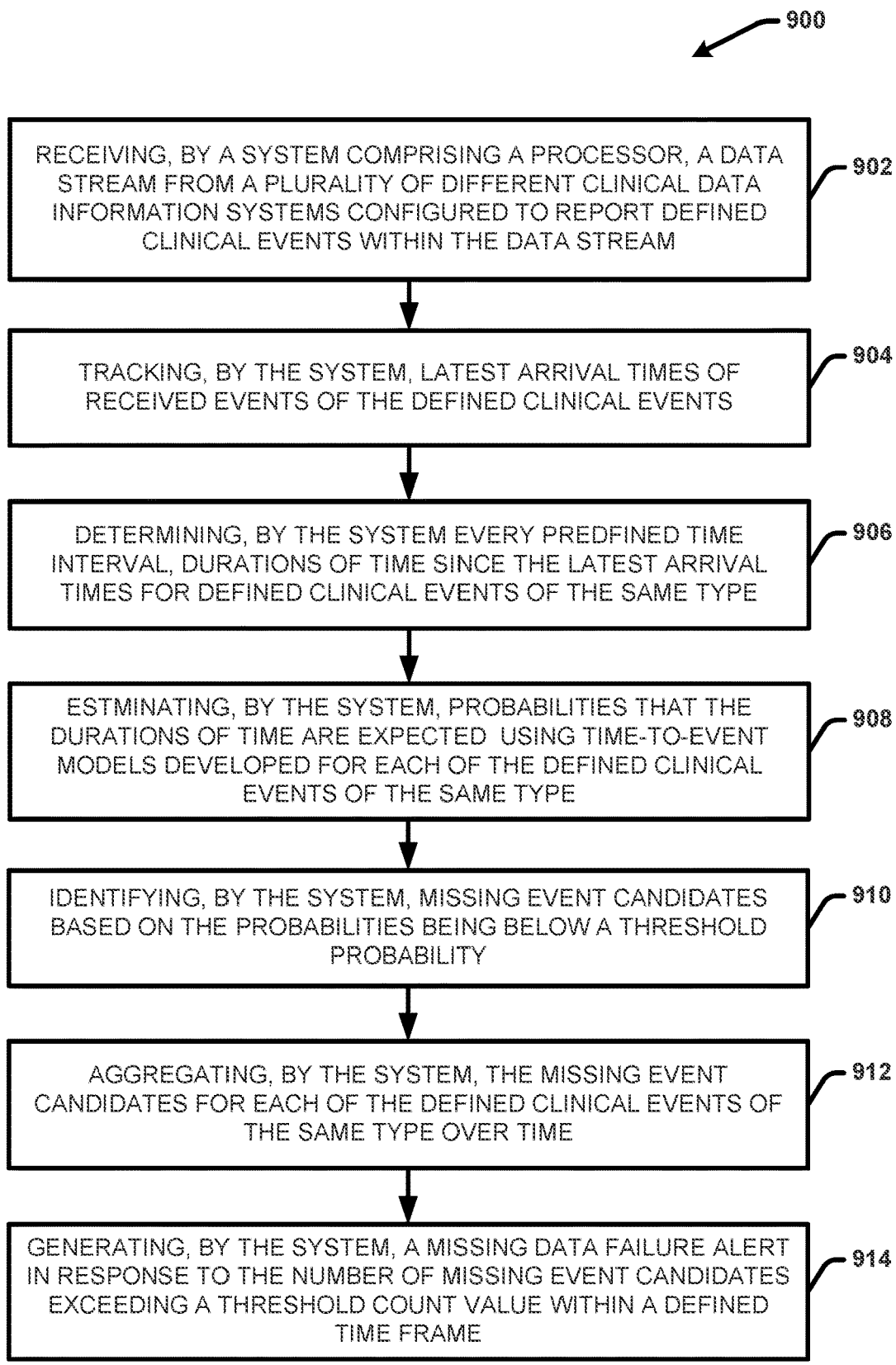
FIG. 9 illustrates a high-level flow diagram of another example computer-implemented method for detecting clinical data drifts in accordance with one or more embodiments of the disclosed subject matter.

FIG. 9 illustrates a high-level flow diagram of another example computer-implemented method 900 for detecting clinical data drifts in accordance with one or more embodiments of the disclosed subject matter. Repetitive description of like elements employed in respective embodiments is omitted for sake of brevity.

In accordance with method 900, at 902, a system operatively coupled to a processor (e.g., system 100, system 200, system 600, or the like) receives comprising a data stream (e.g., clinical event data stream 120) from a plurality of different clinical data information systems (e.g., clinical information systems $212^{1-K}$) configured to report defined clinical events within the data stream (e.g., via reception component 102). At 904, the system tracks latest arrival times of received events of the defined clinical events (e.g., via the reception component 102). At 906 the system determines, every predefined time interval, durations of time since the latest arrival times for defined clinical events of the same type (e.g., via detection component 106). At 908, the system estimates probabilities that the duration of time are expected using time-to-event models (e.g., TTE $112^{1-N}$) developed for each of the defined clinical events of the same type (e.g. via the detection component 106). At 910, the system identifies missing event candidates based on the probabilities being below a threshold probability (e.g., via the detection component 106). At 912, the system aggregates the missing event candidates for each of the defined clinical events of the same type over time, and at 914, the system generates a missing data failure alert in response to the number of missing event candidates exceeding a threshold count value within a defined time frame (e.g., via the alert component 114).

One or more embodiments of the disclosed subject matter are directed to using survival analysis methodology to identify latent data failures in a clinical data stream. The disclosed monitoring systems consider items from a clinical ontology as events and calculate the time between appearances to compute the survival function for each event type. The disclosed systems can utilize both parametric and non-parametric statistical models to compute the survival function. In some embodiments, the parametric model comprises a two-parameter Weibull distribution for fitting the time-to-event data. For medical concepts where a parametric model is proved less accurate, a non-parametric model such as a Parzen windows scheme can alternatively be utilized to compute the survival function.

The disclosed techniques further incorporate a sequential voting mechanism into the scheme. In this regard, every predefined time interval the value of the survival function for all monitored clinical events is computed, and when its value drops below a certain threshold, a count of alert candidates is raised. The count is accumulated until it goes above a count threshold, at which time when an alert is sent to a control center. This scheme adapts to both the severity (number of impacted concepts) and length of time concepts fail to arrive One or more embodiments of the disclosed techniques further use the concept of clustering to improve inference robustness. The main difficulty in modeling the survival function for the missing clinical data concepts stems from the fact that some of these items are rare, (i.e., sent very seldom) while others have multiple synonymous concepts (i.e., they may appear once but then an equal placeholder would show up instead. Both these cases complicate the analysis. This invention utilizes a clinical ontology (e.g., UMLS or the like) in conjunction with manual clustering tools, to cluster related concepts together so that arrival time statistics are computed on entire clusters. The disclosed systems can also consider the hospital ward associated with different clinical events as additional parameter for the clustering.

The disclosed techniques further employ a data-dependent clustering scheme. Since a clinical ontology has a complex graph structure, clustering specific concepts together using only the topology of the graph may be difficult. To this end, the disclosed systems utilize side information to define the proper level of abstraction. Specifically, the disclosed systems utilize the fact that users of the consuming clinical application of the data feed typically query values using their common professional langue. When a term is resolved to a specific clinical concept, (e.g., heart rate or vital signs), the clustering component 602 projects these abstract concepts on the underlying ontology, and once found, all decedents of these concepts are clustered as a same event type. When concept arrive to the detection component 106, the detection component associates them to the proper cluster and applies the corresponding TTE model for that cluster. The disclosed techniques further provide manual control of the level of abstraction. In particular, the system allows users to define concepts of interest, such concepts are used a clustering criterion and allow fine-grained control over the monitored concepts.

The disclosed techniques provide numerous technical advantages. Firstly, monitoring of data failures should reduce the probability of divergence between actual patient data and its aspect in an external application. Secondly, posing the problem of identifying missing data in terms of survival analysis allows utilizing robust statistical tools that were developed for a different domain in a new and useful manner. Thirdly, using a data dependent abstraction scheme reduces the number of clinical concepts that an application monitors which reduces the cost of the solution and simplifies the interpretation of produced alerts. Furthermore, using manual assistance as part of the abstraction scheme allows fine-grained control on the monitored concepts.

The disclosed techniques provide numerous commercial advantages as well. For example, the disclosed techniques simplify the work of operations engineers which are responsible for the ongoing operation of a clinical application configured to consume a clinical data stream. The disclosed techniques further reduce the level of expertise an operations engineer would need when manually monitoring a continuous stream of medical data. Furthermore, by automatically detecting clinical data failure events associated with a clinical data stream transmitted to a clinical application for usage thereof, the disclosed techniques minimize or prevent downstream complications that may result in compromising the applications performance functionality.

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 10, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 10:
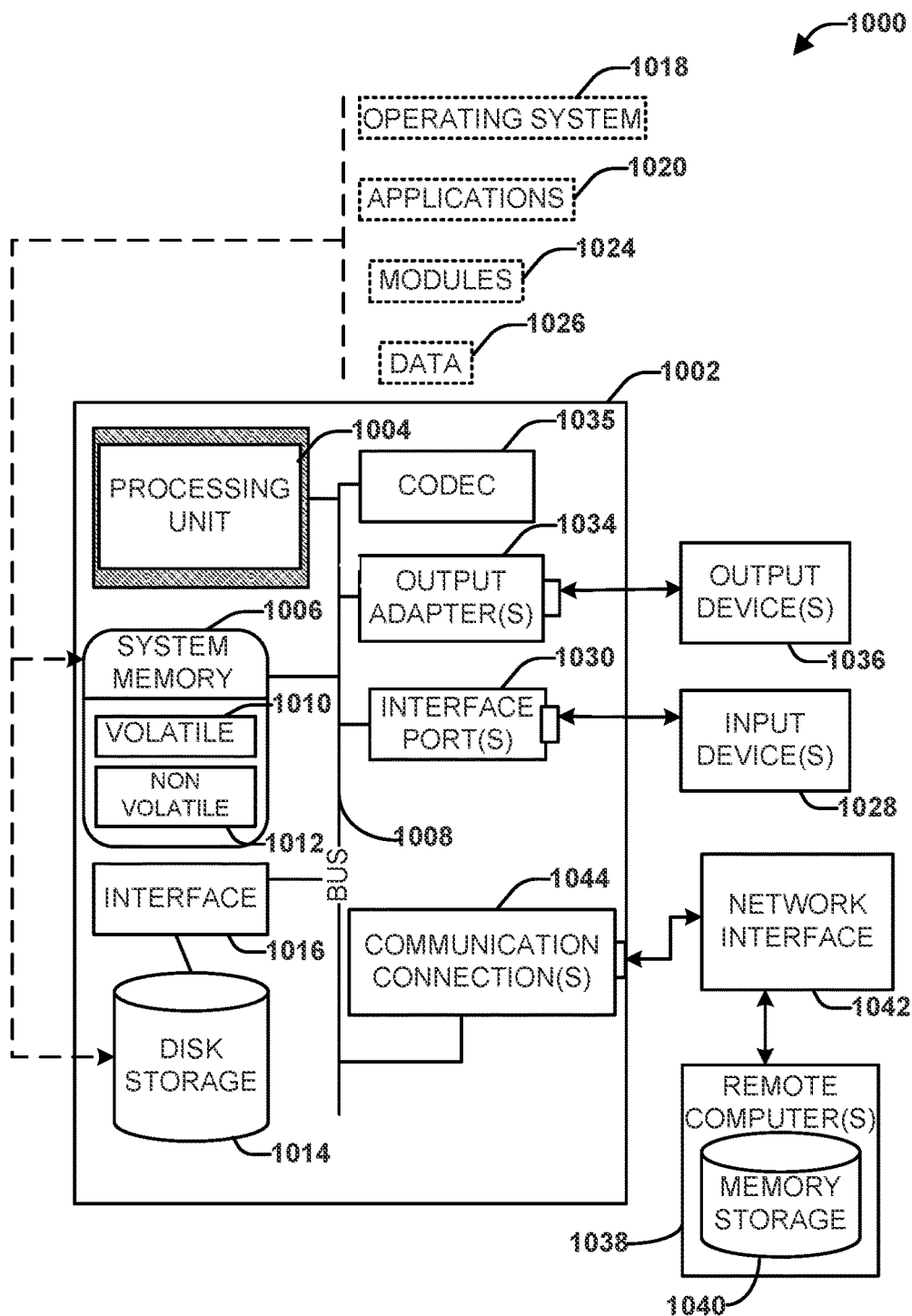
FIG. 10 illustrates a block diagram of an example, non-limiting operating environment in which one or more embodiments described herein can be facilitated.

With reference to FIG. 10, an example environment 1000 for implementing various aspects of the claimed subject matter includes a computer 1002. The computer 1002 includes a processing unit 1004, a system memory 1006, a codec 1035, and a system bus 1008. The system bus 1008 couples system components including, but not limited to, the system memory 1006 to the processing unit 1004. The processing unit 1004 can be any of various available processors. Dual microprocessors and other multiprocessor architectures also can be employed as the processing unit 1004.

The system bus 1008 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13104), and Small Computer Systems Interface (SCSI).

The system memory 1006 includes volatile memory 1010 and non-volatile memory 1012, which can employ one or more of the disclosed memory architectures, in various embodiments. The basic input/output system (BIOS), containing the basic routines to transfer information between elements within the computer 1002, such as during start-up, is stored in non-volatile memory 1012. In addition, according to present innovations, codec 1035 can include at least one of an encoder or decoder, wherein the at least one of an encoder or decoder can consist of hardware, software, or a combination of hardware and software. Although, codec 1035 is depicted as a separate component, codec 1035 can be contained within non-volatile memory 1012. By way of illustration, and not limitation, non-volatile memory 1012 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1012 can employ one or more of the disclosed memory devices, in at least some embodiments. Moreover, non-volatile memory 1012 can be computer memory (e.g., physically integrated with computer 1002 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1010 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1002 can also include removable/non-removable, volatile/non-volatile computer storage medium. FIG. 10 illustrates, for example, disk storage 1014. Disk storage 1014 includes, but is not limited to, devices like a magnetic disk drive, solid state disk (SSD), flash memory card, or memory stick. In addition, disk storage 1014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1014 to the system bus 1008, a removable or non-removable interface is typically used, such as interface 1016. It is appreciated that disk storage 1014 can store information related to an entity. Such information might be stored at or provided to a server or to an application running on an entity device. In one embodiment, the entity can be notified (e.g., by way of output device(s) 1036) of the types of information that are stored to disk storage 1014 or transmitted to the server or application. The entity can be provided the opportunity to opt-in or opt-out of having such information collected or shared with the server or application (e.g., by way of input from input device(s) 1028).

It is to be appreciated that FIG. 10 describes software that acts as an intermediary between entities and the basic computer resources described in the suitable operating environment 1000. Such software includes an operating system 1018. Operating system 1018, which can be stored on disk storage 1014, acts to control and allocate resources of the computer system 1002. Applications 1020 take advantage of the management of resources by operating system 1018 through program modules 1024, and program data 1026, such as the boot/shutdown transaction table and the like, stored either in system memory 1006 or on disk storage 1014. It is to be appreciated that the claimed subject matter can be implemented with various operating systems or combinations of operating systems.

An entity enters commands or information into the computer 1002 through input device(s) 1028. Input devices 1028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1004 through the system bus 1008 via interface port(s) 1030. Interface port(s) 1030 include, for example, a serial port, a parallel port, a game port, and a universal serial bus (USB). Output device(s) 1036 use some of the same type of ports as input device(s) 1028. Thus, for example, a USB port can be used to provide input to computer 1002 and to output information from computer 1002 to an output device 1036. Output adapter 1034 is provided to illustrate that there are some output devices 1036 like monitors, speakers, and printers, among other output devices 1036, which require special adapters. The output adapters 1034 include, by way of illustration and not limitation, video and sound cards that provide a means of connection between the output device 1036 and the system bus 1008. It should be noted that other devices or systems of devices provide both input and output capabilities such as remote computer(s) 1038.

Computer 1002 can operate in a networked environment using logical connections to one or more remote computers, such as remote computer(s) 1038. The remote computer(s) 1038 can be a personal computer, a server, a router, a network PC, a workstation, a microprocessor based appliance, a peer device, a smart phone, a tablet, or other network node, and typically includes many of the elements described relative to computer 1002. For purposes of brevity, only a memory storage device 1040 is illustrated with remote computer(s) 1038. Remote computer(s) 1038 is logically connected to computer 1002 through a network interface 1042 and then connected via communication connection(s) 1044. Network interface 1042 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1044 refers to the hardware/software employed to connect the network interface 1042 to the bus 1008. While communication connection 1044 is shown for illustrative clarity inside computer 1002, it can also be external to computer 1002. The hardware/software necessary for connection to the network interface 1042 includes, for exemplary purposes only, internal and external technologies such as, modems including regular telephone grade modems, cable modems and DSL modems, ISDN adapters, and wired and wireless Ethernet cards, hubs, and routers.

The illustrated aspects of the disclosure may also be practiced in distributed computing environments where certain tasks are performed by remote processing devices that are linked through a communications network. In a distributed computing environment, program modules can be located in both local and remote memory storage devices.

Figure 11:
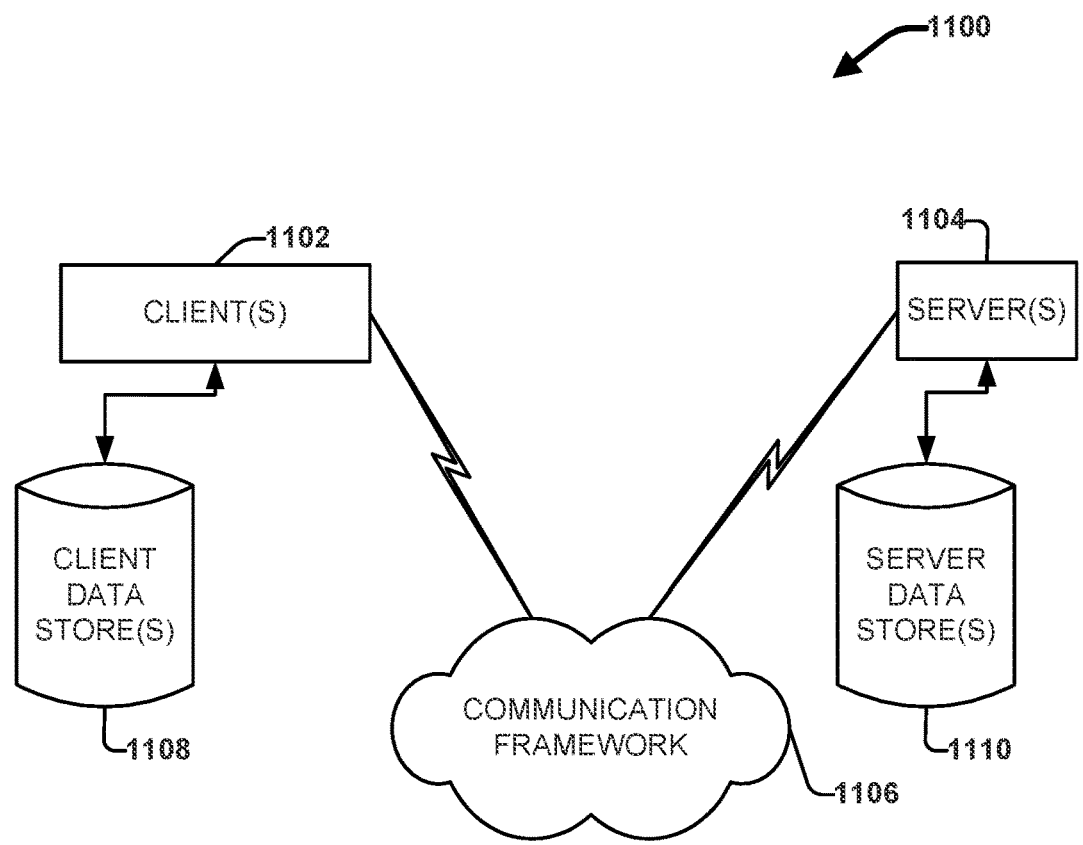
FIG. 11 illustrates a block diagram of another example, non-limiting operating environment in which one or more embodiments described herein can be facilitated.

Referring to FIG. 11, there is illustrated a schematic block diagram of a computing environment 1100 in accordance with this disclosure in which the subject systems (e.g., system 100 and the like), methods and computer readable media can be deployed. The computing environment 1100 includes one or more client(s) 1102 (e.g., laptops, smart phones, PDAs, media players, computers, portable electronic devices, tablets, and the like). The client(s) 1102 can be hardware and/or software (e.g., threads, processes, computing devices). The computing environment 1100 also includes one or more server(s) 1104. The server(s) 1104 can also be hardware or hardware in combination with software (e.g., threads, processes, computing devices). The servers 1104 can house threads to perform transformations by employing aspects of this disclosure, for example. In various embodiments, one or more components, devices, systems, or subsystems of system 100 can be deployed as hardware and/or software at a client 1102 and/or as hardware and/or software deployed at a server 1104. One possible communication between a client 1102 and a server 1104 can be in the form of a data packet transmitted between two or more computer processes wherein the data packet may include healthcare related data, training data, AI models, input data for the AI models, encrypted output data generated by the AI models, and the like. The data packet can include a metadata, e.g., associated contextual information, for example. The computing environment 1100 includes a communication framework 1106 (e.g., a global communication network such as the Internet, or mobile network(s)) that can be employed to facilitate communications between the client(s) 1102 and the server(s) 1104.

Communications can be facilitated via a wired (including optical fiber) and/or wireless technology. The client(s) 1102 include or are operatively connected to one or more client data store(s) 1108 that can be employed to store information local to the client(s) 1102 (e.g., associated contextual information). Similarly, the server(s) 1104 are operatively include or are operatively connected to one or more server data store(s) 1110 that can be employed to store information local to the servers 1104 (e.g., the ML model 104 and trained bias-free versions thereof, the ELF 1011, the training data 116, and the like).

In one embodiment, a client 1102 can transfer an encoded file, in accordance with the disclosed subject matter, to server 1104. Server 1104 can store the file, decode the file, or transmit the file to another client 1102. It is to be appreciated, that a client 1102 can also transfer uncompressed file to a server 1104 can compress the file in accordance with the disclosed subject matter. Likewise, server 1104 can encode video information and transmit the information via communication framework 1106 to one or more clients 1102.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "subsystem" "platform," "layer," "gateway," "interface," "service," "application," "device," and the like, can refer to and/or can include one or more computer-related entities or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
a reception component that:
intercepts a live data comprising medical information identifying clinical events for one or more patients prior to processing of the medical information by a clinical application, wherein the live data stream aggregates the medical information as sent to the system from a plurality of different clinical data information systems;
records reception times of the clinical events as received by the system within the live data stream; and
identifies different event types of the clinical events; and
a detection component that, for each event type of the different event types:
determines time differences between the reception times of respective ones of the clinical events corresponding to the event type;
estimates respective probabilities that the time differences are expected using a time-to-event model tailored to the event type included amongst a plurality of different time-to-event models tailored to the different event types;
detects whether a data failure event associated with the event type has occurred based on the respective probabilities relative to a threshold probability; and
controls the processing of the medical information by the clinical application based on a detection that the data failure event associated with the event type has occurred.

2. The system of claim 1, wherein the computer executable components further comprise:
an alert component that generates a data failure alert in response to the detection of the data failure event and provides the data failure alert to one or more defined entities using one or more electronic notification mechanisms.

3. The system of claim 1, wherein the time-to-event model employs a survival analysis function to determine the probabilities that the time differences are expected.

4. The system of claim 3, wherein the time-to-event model comprises a parametric statistical model that models a distribution of previously recorded time differences between historical reception times of historical clinical events corresponding to the event type within the live data stream, and wherein the detection component employs the parametric statistical model to compute the survival function and estimate the probabilities.

5. The system of claim 4, wherein the parametric statistical model comprises a Weibull distribution model.

6. The system of claim 3, wherein the time-to-event model comprises a non-parametric statistical model that models a distribution of previously recorded time differences between historical reception times of historical clinical events corresponding to the event type within the live data stream, and wherein the detection component employs the parametric statistical model to compute the survival function and estimate the probabilities.

7. The system of claim 1, wherein the time-to-event model comprises a parametric statistical model that models a distribution of previously recorded time differences between historical reception times of historical clinical events corresponding to the event type within the live data stream, and wherein the computer executable components further comprise:
a model development component that generates the time-to-event model using the distribution.

8. The system of claim 1, wherein the detection component determines the time differences and estimates the probabilities that the time differences are expected using the time-to-event model every predefined time interval.

9. The system of claim 8, wherein the detection component identifies missing event candidates based on the probabilities being below the threshold probability and wherein the detection component aggregates the missing event candidates for the event type over time, and wherein the computer executable components further comprise:
an alert component that generates missing data failure alerts in response to the number of missing event candidates exceeding a threshold count value within a defined time frame.

10. The system of claim 8, wherein the detection component aggregates the probabilities over sequential time intervals of the predefined time interval, and wherein the computer executable components further comprise:
an alert component that generates a missing data failure alert based on the aggregated probabilities exceeding a threshold value.

11. The system of claim 1, wherein the computer executable components further comprise:
a clustering component that determines the different event types based on a defined clinical ontology, wherein the clustering component clusters related clinical concepts in the defined clinical ontology into a same event type of the different event types; and
a feedback component that receives input defining one or more clustering criteria for clustering the related clinical concepts, and wherein the clustering component applies the one or more clustering criteria to cluster the related clinical concepts.

12. A method comprising:
intercepting, by a system comprising a processor, a live data stream comprising medical information for one or more patients prior to processing of the medical information by a clinical application, wherein the live data stream aggregates the medical information as sent to the system from a plurality of different clinical data information systems;
identifying, by the system, different types of event data objects included in the live data stream corresponding to different clinical event types;
recording, by the system, reception times of the event data objects by the system;
for each event type of the different clinical event types:
determining, by the system, time differences between the reception times of respective ones of the event data objects corresponding to the event type;
estimating, by the system, probabilities that the time differences are expected using a time-to-event model tailored to the event type included amongst a plurality of different time-to-event models tailored to the different event types;

detecting, by the system, a data failure event associated with the event type based on the probability relative to a threshold probability; and controlling, by the system, the processing of the medical information by the clinical application based on the detecting.

13. The method of claim 12, further comprising:
generating, by the system, a data failure alert in response to detection of the data failure event; and
providing, by the system, the data failure alert to one or more defined entities using one or more electronic notification mechanisms.

14. The method of claim 12, wherein the time-to-event model employs a survival analysis function to determine the probabilities that the time differences are expected.

15. The method of claim 14, wherein the time-to-event model comprises a statistical model that models a distribution of previously recorded time differences between historical reception times of historical clinical events corresponding to the event type within the live data stream, and wherein the detection component employs the parametric statistical model to compute the survival function and estimate the probabilities, and wherein the method further comprises:
generating, by the system, the time-to-event model using the distribution and one or more machine learning techniques.

16. The method of claim 12, wherein the detecting comprises determining the time differences and estimating the probabilities that the time differences are expected using the time-to-event model every predefined time interval.

17. The method of claim 16, wherein the detecting further comprises:
identifying, by the system, missing event candidates based on the probabilities being below the threshold probability;
aggregating, by the system, the missing event candidates over time; and
generating, by the system, a missing data failure alert in response to the number of missing event candidates exceeding a threshold count value within a defined time frame.

18. The method of claim of 12, further comprising:
determining, by the system, the different clinical event types for monitoring in the live data stream based on a defined clinical ontology; and
clustering, by the system, related clinical concepts in the defined clinical ontology into a same event type of the different clinical event types.

19. A non-transitory machine-readable storage medium, comprising executable instructions that, when executed by a processor, facilitate performance of operations, comprising:
intercepting a live data stream comprising medical information for one or more patients prior to processing of the medical information by a clinical application, wherein the live data stream aggregates the medical information as sent to the system from a plurality of different clinical data information systems;
identifying different types of event data objects included in the live data stream corresponding to different clinical event types;
recording reception times of the event data objects by the system;
for each event type of the different clinical event types:
determining time differences between the reception times of respective ones of the event data objects corresponding to the event type;
estimating probabilities that the time differences are expected using a time-to-event model tailored to the event type included amongst a plurality of different time-to-event models tailored to the different event types;
detecting a data failure event associated with the event type based on the probability relative to a threshold probability; and
controlling the processing of the medical information by the clinical application based on the detecting.

20. The non-transitory machine-readable storage medium of claim 19, wherein the operations further comprise:
generating a data failure alert in response to a detection of the data failure event; and
providing the data failure alert to one or more defined entities using one or more electronic notification mechanisms.

* * * * *